United States Patent
Coffeen et al.

(10) Patent No.: US 11,937,783 B2
(45) Date of Patent: Mar. 26, 2024

(54) SYSTEMS AND METHODS FOR INTRAOPERATIVE SURGICAL SCOPE CLEANING

(71) Applicant: Stryker Corporation, Kalamazoo, MI (US)

(72) Inventors: Jared Coffeen, Hollister, CA (US); Theodore Leclere, San Francisco, CA (US); Eric Huynh, San Ramon, CA (US)

(73) Assignee: Stryker Corporation, Kalamazoo, MI (US)

( * ) Notice: Subject to any disclaimer, the term of this patent is extended or adjusted under 35 U.S.C. 154(b) by 7 days.

(21) Appl. No.: 16/886,590

(22) Filed: May 28, 2020

(65) Prior Publication Data
US 2020/0375444 A1 Dec. 3, 2020

Related U.S. Application Data

(60) Provisional application No. 62/854,165, filed on May 29, 2019.

(51) Int. Cl.
*A61B 1/00* (2006.01)
*A61B 1/015* (2006.01)
(Continued)

(52) U.S. Cl.
CPC .......... *A61B 1/015* (2013.01); *A61B 1/00006* (2013.01); *A61B 1/00009* (2013.01);
(Continued)

(58) Field of Classification Search
CPC . A61B 1/126; A61B 1/00006; A61B 1/00009; A61B 1/00055; A61B 1/00091;
(Continued)

(56) References Cited

U.S. PATENT DOCUMENTS

| 4,279,246 A | 7/1981 | Chikama |
| 5,386,817 A | 2/1995 | Jones |

(Continued)

FOREIGN PATENT DOCUMENTS

| WO | 2010027381 A1 | 3/2010 |
| WO | 2018071821 A1 | 4/2018 |

OTHER PUBLICATIONS

International Search Report and Written Opinion of the International Searching Authority dated Oct. 26, 2020, for International Patent Application No. PCT/US2020/034878, filed May 28, 2020, 17 pages.

(Continued)

*Primary Examiner* — Timothy J Neal
(74) *Attorney, Agent, or Firm* — Morrison & Foerster LLP

(57) ABSTRACT

A system for cleaning a surgical scope of an endoscopic imager includes a control system communicatively connected to an apparatus for supplying fluids to a surgical scope cleaner, the control system configured to receive one or more images of a surgical field generated by the endoscopic imager, detect a deposit on a lens of the surgical scope by analyzing the one or more images, and send a command to the apparatus to provide one or more fluids to the surgical field for cleaning the surgical scope.

18 Claims, 27 Drawing Sheets

(51) Int. Cl.
*A61B 1/12* (2006.01)
*A61M 13/00* (2006.01)

(52) U.S. Cl.
CPC ...... *A61B 1/00055* (2013.01); *A61B 1/00091* (2013.01); *A61B 1/00128* (2013.01); *A61B 1/0014* (2013.01); *A61B 1/126* (2013.01); *A61M 13/003* (2013.01)

(58) Field of Classification Search
CPC ... A61B 1/00128; A61B 1/0014; A61B 1/015; A61B 1/04; A61B 1/00068; A61B 1/00119; A61B 1/00135; A61B 1/00105; A61B 1/00144; A61B 1/05; A61B 1/12; A61B 1/121; A61B 1/127; A61B 50/30; A61M 13/003; G02B 23/2484; G02B 27/0006
USPC .......................................... 600/121, 157, 158
See application file for complete search history.

(56) References Cited

U.S. PATENT DOCUMENTS

| | | | |
|---|---|---|---|
| 5,464,008 A | 11/1995 | Kim | |
| 5,518,502 A | 5/1996 | Kaplan | |
| 5,605,532 A | 2/1997 | Schermerhorn | |
| 6,062,429 A | 5/2000 | West | |
| 6,354,992 B1 | 3/2002 | Kato | |
| 6,447,446 B1 | 9/2002 | Smith | |
| 6,595,915 B2 | 7/2003 | Akiba | |
| 6,638,214 B2 | 10/2003 | Akiba | |
| 6,712,479 B1 | 3/2004 | Seitzinger | |
| 6,755,782 B2 | 6/2004 | Ogawa | |
| 7,811,228 B2 | 10/2010 | Adams | |
| 8,047,215 B1 | 11/2011 | Sasaki | |
| 8,079,952 B2 | 12/2011 | Fujimoto | |
| 8,096,944 B2 | 1/2012 | Harrel | |
| 8,185,997 B2 | 5/2012 | Heck | |
| 8,397,335 B2 | 3/2013 | Gordin | |
| 8,979,738 B2 | 3/2015 | Hsu | |
| 9,241,610 B2 | 1/2016 | Hsu | |
| 2005/0222499 A1* | 10/2005 | Banik | A61B 1/0676 600/156 |
| 2006/0069306 A1* | 3/2006 | Banik | A61B 1/000095 600/117 |
| 2006/0106285 A1* | 5/2006 | Boulais | A61B 1/128 600/156 |
| 2007/0255106 A1* | 11/2007 | Kawanishi | A61B 1/3132 600/159 |
| 2008/0081948 A1 | 4/2008 | Weisenburgh, II | |
| 2008/0188714 A1* | 8/2008 | McCaffrey | A61B 1/121 600/157 |
| 2008/0319266 A1 | 12/2008 | Poll | |
| 2009/0105543 A1 | 4/2009 | Miller | |
| 2009/0118586 A1 | 5/2009 | Griffin | |
| 2009/0264703 A1 | 10/2009 | Pribanic | |
| 2010/0174144 A1 | 7/2010 | Hsu | |
| 2010/0198014 A1 | 8/2010 | Poll | |
| 2010/0228087 A1* | 9/2010 | Shener | A61M 5/142 600/109 |
| 2012/0059222 A1* | 3/2012 | Yoshida | A61B 1/00091 600/157 |
| 2012/0178995 A1 | 7/2012 | Newton, IV | |
| 2012/0197084 A1* | 8/2012 | Drach | A61B 1/0008 600/123 |
| 2013/0053639 A1 | 2/2013 | Ihde, II | |
| 2013/0217970 A1 | 8/2013 | Weisenburgh, II | |
| 2013/0331730 A1* | 12/2013 | Fenech | A61B 1/00006 600/560 |
| 2014/0034082 A1 | 2/2014 | Hurst | |
| 2014/0200406 A1 | 7/2014 | Bennett | |
| 2014/0246051 A1 | 9/2014 | Hurst | |
| 2014/0249370 A1 | 9/2014 | Hurst | |
| 2014/0261579 A1 | 9/2014 | Jenkins | |
| 2014/0275787 A1* | 9/2014 | Miyamoto | A61B 1/00135 600/157 |
| 2014/0371763 A1* | 12/2014 | Poll | A61B 34/30 606/130 |
| 2015/0201826 A1 | 7/2015 | Hsu | |
| 2015/0238127 A1* | 8/2015 | Saito | A61M 31/005 600/431 |
| 2016/0128551 A1 | 5/2016 | Hsu | |
| 2017/0238795 A1* | 8/2017 | Blumenkranz | A61B 1/00091 |
| 2018/0008138 A1* | 1/2018 | Thommen | A61B 17/3423 |
| 2018/0014720 A1 | 1/2018 | Leuthardt et al. | |
| 2018/0042453 A1* | 2/2018 | Hino | G02B 23/2415 |
| 2018/0078120 A1* | 3/2018 | Poll | A61B 1/00105 |
| 2018/0214016 A1* | 8/2018 | Thommen | A61B 17/025 |
| 2018/0361055 A1* | 12/2018 | Pereira | A61M 3/0216 |
| 2019/0125176 A1* | 5/2019 | Burt | A61B 1/00006 |
| 2019/0167071 A1* | 6/2019 | Yokouchi | A61B 1/00055 |
| 2019/0274528 A1* | 9/2019 | Petroff | A61B 5/0084 |
| 2020/0107889 A1* | 4/2020 | Gliner | A61B 5/062 |
| 2020/0268240 A1* | 8/2020 | Blumenkranz | B08B 5/02 |
| 2022/0104697 A1* | 4/2022 | Blumenkranz | A61B 1/00091 |

OTHER PUBLICATIONS

Invitation to Pay Additional Fees dated Aug. 26, 2020, for International Patent Application No. PCT/US2020/034878, filed May 28, 2020, 11 pages.

* cited by examiner

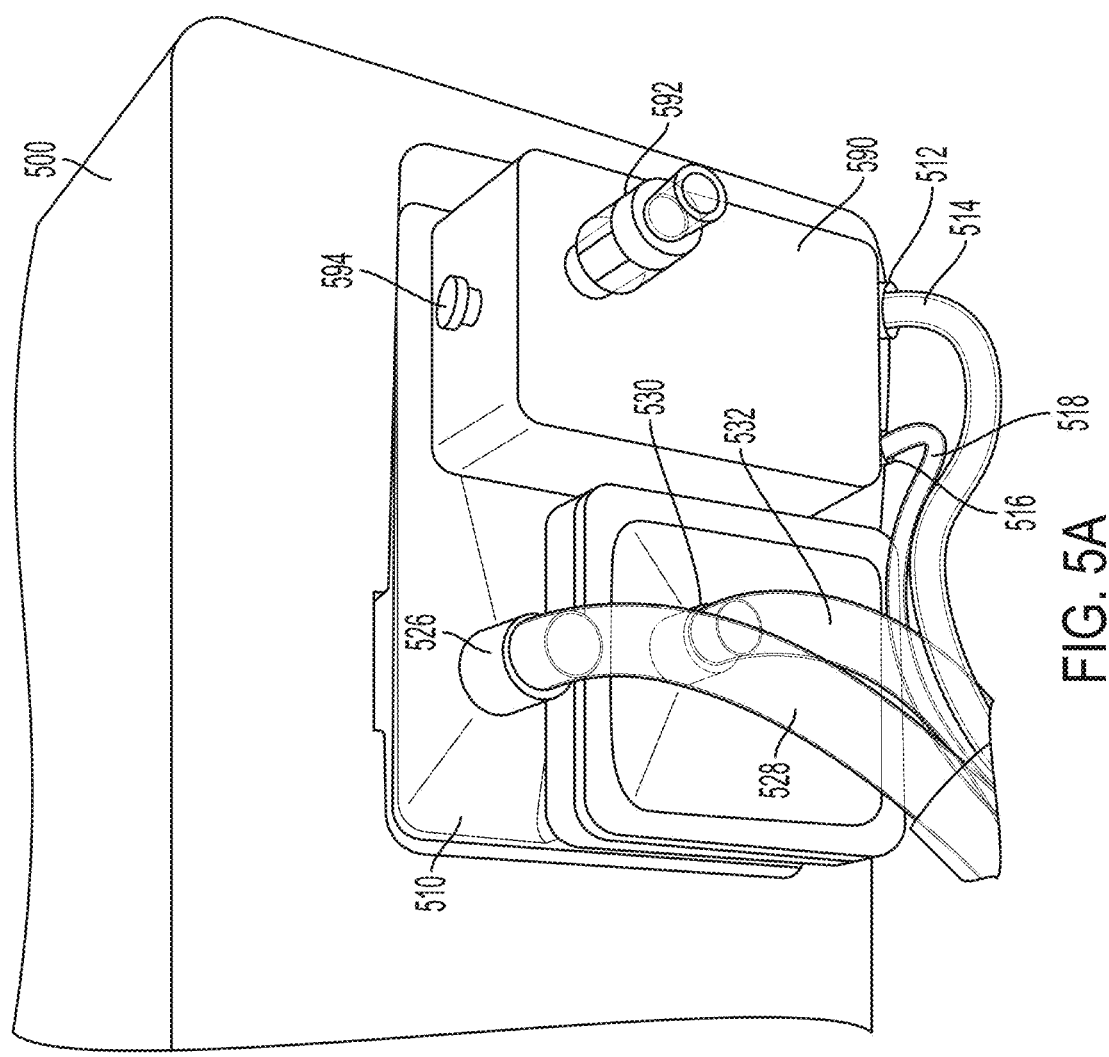

SYSTEMS AND METHODS FOR INTRAOPERATIVE SURGICAL SCOPE CLEANING

CROSS-REFERENCE TO RELATED APPLICATIONS

This application claims the benefit of U.S. Provisional Application No. 62/854,165, filed May 29, 2019, the entire contents of which are hereby incorporated by reference herein.

FIELD OF THE INVENTION

The present disclosure relates generally to endoscopic surgery, and more particularly to cleaning a surgical scope during a surgical procedure.

BACKGROUND OF THE INVENTION

Although laparoscopic surgery has been performed going back as far as 1901, it became more widespread upon the introduction of the rigid laparoscope with a rod lens optical train and glass fiber optic illumination in the mid 1980's. Since then, laparoscopic surgery has evolved into the standard of care for many types of abdominal surgery.

Since a surgeon is dependent on the image provided by the laparoscope, the surgeon's performance is impaired if the lens at the distal end of the laparoscope is not kept clean while in the surgical cavity. For example, the surgeon can have difficulty viewing the surgical field when any of the following occurs: the surface temperature of the lens is lower than the temperature of the surgical cavity and condensation forms on the lens, which is referred to as "scope fogging"; the lens touches tissue in the surgical cavity during the course of the surgery and becomes soiled with fat, blood, pieces of tissue, bile, etc., which is referred to as "scope smudging"; fluids splash or squirt at the laparoscope during the surgery and accumulate on the lens, such as blood from a perforated artery, irrigation fluid while washing the surgical site with pressurized saline, etc., which is also referred to as "scope smudging"; and the laparoscope is passed through a trocar in order to enter the surgical cavity and the lens touches blood, fat, pieces of tissue, or lubricant from the seals of the trocar, which is also referred to as "scope smudging".

Many attempts have been made to address the problems of lens fogging and scope smudging. However, these attempts have been largely unsuccessful and surgeons continue to remove the laparoscope from the surgical cavity for cleaning and then subsequently re-insert the laparoscope into the surgical cavity to continue the surgery. Often, re-insertion into the surgical cavity through a trocar smudges the scope again, and the cleaning process must be repeated until the surgeon is able to obtain a clear image of the surgical cavity.

Attempts to solve scope smudging and fogging have often been ineffective for several reasons. Designs with lens-cleaning features built into the scope itself have the benefit of not requiring the surgeon to remove the scope from the surgical cavity during surgery but can substantially complicate the design of the scope and make cleaning and sterilizing the scope difficult and can affect the scope's reliability and useful life. Designs having a mechanism for mechanically cleaning the scope, such as wipers or sponges, have difficulty keeping the mechanism clean and dry enough to be effective at cleaning the lens over the course of a surgery. Such designs may also require the surgeon to move the scope back and forth past the cleaning mechanism, which can distract the surgeon from the surgery.

Designs that have a sheath for preventing the lens from being contacted by fluids and debris substantially complicate the process of cleaning the lens should the lens be smudged because access to the lens is made more difficult, often requiring removal of the sheath to properly clean the lens. Designs that include a sheath that, together with the outer surface of the scope, forms a lumen for fluid or gas to pass through for cleaning the lens can generally only be configured to work with a particular make and model of laparoscope because the fit between the scope and the sheath is critical. The manufacturing tolerances of the scope and the sheath as well as the fact that the mating surface of one or the other over time will get damaged due to reprocessing by hospital staff can make such design impractical.

Designs that have a film that protects the lens from making contact with the fluids and tissue during surgery can suffer from a number of drawbacks. Anything positioned in front of the lens of the scope will cause some level of image degradation. The film may not always be able to seal perfectly and prevent the lens from getting smudged and fluid from penetrating the sheath and remaining there, which can cause any new film that is advanced in front of the lens to also become smudged. Further, the film may not help prevent fogging, which means that the scope must be properly warmed directly before installing the sheath and inserting into the surgical cavity. If the scope is removed during the surgery for any reason, it must be warmed again before being reinserted into the surgical cavity or else it will get fogged again.

Designs that spray a cleaner at the lens and suction the waste away have not been successful in laparoscopic surgery since it is often difficult to rely on a suction flow to always pull the tiny drops of fluid across the lens for removal due to the surface tension between the glass and the fluid droplets.

SUMMARY OF THE INVENTION

According to some embodiments, a surgical scope cleaner includes a sheath that is configured to slide over the surgical scope and at least one nozzle located at the end of the sheath for spraying a cleaning liquid and a gas onto the lens at the end of the surgical scope to clean the lens. The sheath is configured to fit over the tube of the scope and through the lumen of a trocar, so that the sheath remains in place on the scope during the surgical procedure. When the lens becomes smudged and/or fogged, liquid can be sprayed onto the lens and then the gas can be blown at the lens to remove any remaining liquid. The sheath includes conduits for the liquid and gas that may be formed into one side of the wall of the sheath to maintain a small diameter so that the sheath can fit through a standard size trocar while mounted to a standard size scope.

The surgical scope cleaner can be connected to a fluid management apparatus that can control the delivery of the liquid and gas from the scope cleaner to the lens. The fluid management apparatus can also manage the supply of other fluids to the surgical field, including for example, serving as an insufflator for supplying insufflating gas for insufflating the surgical cavity. An integrated tube set can be used to transport fluids between the surgical field and the apparatus and/or other equipment, which can reduce the clutter in the surgical field. The tube set can include a connector for connecting at least some of the tubes of the tube set to the apparatus for efficient pre-operative set-up.

According to some embodiments, an apparatus for cleaning a surgical scope includes a sheath for removably receiving a tube of the surgical scope, the sheath including a wall defining a channel for receiving the tube, where a distal portion of the wall is configured to extend only partially around a circumference of the tube, a first conduit that defines a liquid flow path, and a second conduit that defines a gas flow path; and at least one nozzle located at a distal end of the distal portion of the wall and configured for directing a flow of liquid from the first conduit across a lens of the surgical scope and directing a flow of gas from the second conduit across the lens of the surgical scope to clear the liquid from the lens.

In any of these embodiments, at least the distal portion of the wall may be configured for positioning in a trocar during use.

In any of these embodiments, the apparatus may further include a first port for connecting a liquid supply line to the first conduit and a second port for connecting a gas supply line to the second conduit.

In any of these embodiments, the liquid flow path from the first port to the first nozzle and the gas flow path from the second port to the second nozzle may be valve-free.

In any of these embodiments, the apparatus may further include a receiver located at a proximal end of the sheath for receiving a housing of the surgical scope.

In any of these embodiments, a proximal portion of the wall may be configured to extend completely around a circumference of the tube of the surgical scope.

In any of these embodiments, only the distal portion of the wall may be positioned in the trocar during use.

In any of these embodiments, the distal end of the wall may be further away from a longitudinal axis of the tube of the surgical scope than a proximal end of the wall when the surgical scope is received in the sheath.

In any of these embodiments, the wall may be configured so that the distal portion of the wall can bend toward the longitudinal axis of the tube of the surgical scope during insertion into a trocar and can then return to a position further away from the longitudinal axis of the tube of the surgical scope when the distal portion is through the trocar.

In any of these embodiments, the first conduit may be adjacent to the second conduit.

In any of these embodiments, the at least one nozzle may be a first nozzle that is adjacent to a second nozzle.

In any of these embodiments, the first and second conduits may be formed into a thickness of the wall.

In any of these embodiments, the thickness of the wall may be non-uniform around a circumference of at least a portion of the wall.

In any of these embodiments, the at least one nozzle may be located for cleaning the surgical scope while the surgical scope views a surgical field.

In any of these embodiments, the at least one nozzle may be located so that a field of view of the surgical scope is unobstructed.

In any of these embodiments, the at least one nozzle may be located at a distal end of the sheath.

In any of these embodiments, at least the sheath may be made of a plastic.

In any of these embodiments, the apparatus may be disposable.

According to some embodiments, a method for cleaning a surgical scope while the surgical scope is inserted in a surgical cavity includes inserting the surgical scope into a sheath of a surgical scope cleaner, wherein a distal portion of the sheath extends only partially around a tube of the surgical scope; inserting the surgical scope and sheath into the surgical cavity; observing the surgical cavity using the surgical scope that is inserted in the sheath of the surgical scope cleaner; and cleaning deposits from a lens of the surgical scope by: spraying the lens with a liquid from at least one nozzle of the surgical scope cleaner to remove the deposits from the lens, and blowing the lens of the surgical scope with a gas from the at least one nozzle of the surgical scope cleaner to remove the liquid from the lens.

In any of these embodiments, the sheath may include a first conduit that defines a liquid flow path, and a second conduit that defines a gas flow path.

In any of these embodiments, inserting the surgical scope and sheath into the surgical cavity may include inserting the surgical scope and sheath through a trocar.

In any of these embodiments, the deposits may be cleaned from the lens in response to a user input to an endoscopic imager connected to the surgical scope.

In any of these embodiments, the deposits may be cleaned from the lens based on a detection of the deposits by an image processing system via one or more images generated by an endoscopic imager connected to the surgical scope.

In any of these embodiments, the deposits may include condensation.

In any of these embodiments, the deposits may include one or more of bodily fluids, tissue, and one or more fluids introduced into the surgical cavity.

In any of these embodiments, the lens may be sprayed with the liquid for a first predetermined period and the lens may be blown with the gas for a second predetermined period.

According to some embodiments, an apparatus for supplying fluids to a surgical field includes a gas inlet port for connecting a supply line for supplying a gas to the apparatus; a first outlet port for supplying a first flow of the gas for insufflating a surgical cavity during a surgical procedure; an actuator for controlling a liquid flow for cleaning a surgical scope during the surgical procedure; and a second outlet port for supplying a second flow of the gas for clearing liquid from the surgical scope during the surgical procedure.

In any of these embodiments, the actuator may include a solenoid.

In any of these embodiments, the actuator may be configured to close a flow path in the apparatus.

In any of these embodiments, the actuator may be configured close a flow path in a device connected to the apparatus.

In any of these embodiments, the actuator may actuate a valve in the apparatus.

In any of these embodiments, the apparatus may include a third outlet port for pressurizing a reservoir for the liquid flow.

In any of these embodiments, the first, second, and third outlets may be located in a receiver configured for receiving a connector that connects the apparatus to a tube set for supplying fluids to the surgical field.

In any of these embodiments, the actuator may be configured to close off a flow path for the liquid flow in the connector.

In any of these embodiments, the actuator may actuate a valve in the connector for controlling the liquid flow.

In any of these embodiments, the apparatus may include a motor for driving a pump in the connector.

In any of these embodiments, the actuator may be configured to pinch a liquid flow tube for controlling the liquid flow.

In any of these embodiments, the apparatus may further include a second actuator that is configured to pinch a gas flow tube for controlling the second flow of the gas.

In any of these embodiments, the apparatus may further include a first regulator for supplying the first flow of the gas at a first pressure and a second regulator for pressurizing a reservoir for the liquid flow at a second pressure that is different than the first pressure.

In any of these embodiments, the apparatus may further include a liquid inlet port for receiving the liquid from a reservoir.

In any of these embodiments, the apparatus may further include a gas inlet port for receiving a gas flow from the surgical cavity during the surgical procedure.

In any of these embodiments, the apparatus may further include a communication port for receiving control commands for actuating the actuator.

In any of these embodiments, the apparatus may further include a controller that is configured to control the liquid flow and the second flow of the gas for cleaning the surgical scope.

In any of these embodiments, the controller may be configured to control a cleaning sequence that includes providing the liquid flow for a first period and providing the second flow of the gas for a second period that is at least partially subsequent to the first period.

In any of these embodiments, the apparatus may be configured for receiving a scope cleaning command from an external system.

In any of these embodiments, the external system may include an image processing system.

In any of these embodiments, the external system may include an endoscopic imager comprising the surgical scope.

In any of these embodiments, the apparatus may further include a user interface for receiving a scope cleaning command from a user.

According to some embodiments, a tube set for supplying fluids to a surgical field includes a connector for connecting the tube set to a fluid supply system; a first supply tube for supplying a first gas flow for insufflating a surgical cavity during a surgical procedure, the first supply tube connected to a first port of the connector; a second supply tube for supplying a liquid for cleaning a surgical scope during the surgical procedure, the second supply tube connected to a second port of the connector; and a third supply tube for supplying a second gas flow for clearing the liquid from the surgical scope during the surgical procedure, the third supply tube connected to a third port of the connector.

In any of these embodiments, the tube set further includes an outer tube for housing the first, second, and third supply tubes.

In any of these embodiments, the tube set may be a single use tube set.

In any of these embodiments, the first, second, and third supply tubes may be made of plastic.

In any of these embodiments, a length of the tube set may allow one end of the tube set to extend into the surgical field and an opposite end to connect to at least one piece of equipment for supplying a fluid to the surgical field.

In any of these embodiments, the tube set may further include an evacuation tube for evacuating smoke from the surgical cavity during the surgical procedure.

In any of these embodiments, the connector may include at least one filter for filtering smoke evacuated from the surgical cavity.

In any of these embodiments, the connector may include a housing that comprises ports for connecting the first supply tube and the third supply tube to the fluid supply system.

In any of these embodiments, the housing may be configured for latching to a receiver of the fluid supply system.

In any of these embodiments, the tube set may further include a reservoir connection tube for connecting to a reservoir of the liquid for cleaning the surgical scope.

In any of these embodiments, the tube set may further include a pressurization tube for supplying pressurization gas for pressurizing the reservoir.

In any of these embodiments, the pressurization tube may be connectable to a pressurization sleeve for pressurizing a bag comprising the reservoir.

In any of these embodiments, the connector may include a valve for controlling flow from the reservoir connection tube to the second supply tube.

In any of these embodiments, the connector may include a reservoir of the liquid for cleaning the surgical scope.

In any of these embodiments, the tube set may further include an irrigation supply line for supplying the liquid for irrigating the surgical cavity, the irrigation supply line connected to the connector.

In any of these embodiments, the tube set may further include a surgical scope cleaning apparatus that is connected to the second and third supply tubes for cleaning the surgical scope during the surgical procedure.

According to some embodiments, a method for supplying fluids to a surgical field includes connecting a connector of a tube set to a fluid supply system, wherein the tube set comprises a first supply tube connected to a first port of the connector, a second supply tube connected to a second port of the connector, and a third supply tube connected to a third port of the connector; supplying a first gas flow for insufflating a surgical cavity during a surgical procedure via the first supply tube; supplying a liquid for cleaning a surgical scope during the surgical procedure via the second supply tube; and supplying a second gas flow for clearing the liquid from the surgical scope during the surgical procedure via the third supply tube.

In any of these embodiments, the first gas flow and the second gas flow may include the same gas.

In any of these embodiments, the tube set may be a sterilized and packaged tube set.

In any of these embodiments, the tube set may be a single use tube set.

In any of these embodiments, the method may further include evacuating the surgical cavity via an evacuation tube connected to a fourth port of the connector.

According to some embodiments, a system for cleaning a surgical scope of an endoscopic imager includes a control system communicatively connected to an apparatus for supplying fluids to a surgical scope cleaner, the control system configured to: receive one or more images of a surgical field generated by the endoscopic imager, detect a deposit on a lens of the surgical scope by analyzing the one or more images, and send a command to the apparatus to provide one or more fluids to the surgical field for cleaning the surgical scope.

In any of these embodiments, the system may include the apparatus and the apparatus may be configured for supplying a liquid flow and a gas flow for a surgical field for cleaning a lens of the surgical scope during a surgical procedure.

In any of these embodiments, the apparatus may be configured to perform a cleaning sequence in response to receiving the command from the control system, the cleaning sequence including supplying the liquid flow for a first period and supplying the gas flow for a second period that is at least partially subsequent to the first period.

In any of these embodiments, the control system may be configured for analyzing the one or more images at least partially by comparing at least one of the one or more images to at least one previously generated image.

In any of these embodiments, the control system may be further configured to: provide a notification to a user that a deposit on the lens has been detected, receive a confirmation from a user to clean the surgical scope, and in response to receiving the confirmation from the user, send the command to the apparatus to provide the one or more fluids to the surgical field for cleaning the surgical scope.

In any of these embodiments, the confirmation from the user may be received from an endoscopic imager that is communicatively connected to the control system.

In any of these embodiments, the apparatus may be configured for supplying an insufflating gas flow to the surgical field.

According to some embodiments, a method for cleaning a surgical scope of an endoscopic imager via a control system communicatively connected to an apparatus for supplying fluids to a surgical scope cleaner includes receiving one or more images of a surgical field from the endoscopic imager at the control system; detecting by the control system a deposit on a lens of the surgical scope by analyzing the one or more images; and sending a command from the control system to the apparatus to provide one or more fluids to the surgical field for cleaning the surgical scope.

In any of these embodiments, the method may further include, in response to receiving the command from the control system, supplying a liquid flow and a gas flow from the apparatus for cleaning a lens of the surgical scope during a surgical procedure.

In any of these embodiments, supplying the liquid flow and the gas flow may include supplying the liquid flow for a first period and supplying the gas flow for a second period that is at least partially subsequent to the first period.

In any of these embodiments, the method further includes providing a notification to a user that a deposit on the lens has been detected; receiving a confirmation from a user to clean the surgical scope; and in response to receiving the confirmation from the user, sending the command to the apparatus to provide the liquid flow and the gas flow to the surgical field for cleaning the lens of the surgical scope.

In any of these embodiments, the confirmation from the user may be received from an endoscopic imager that is communicatively connected to the control system.

In any of these embodiments, the method may further include supplying an insufflating gas flow from the apparatus to the surgical field.

According to some embodiments, an endoscope includes a main body comprising a light port and at least one fluid port; and a shaft extending distally from the main body and including: a first wall portion that houses fiber optics for directing light introduced through the light port, a second wall portion extending partially around the first wall portion, an optical component located at a distal end of the shaft, at least one fluid channel located between the first wall portion and the second wall portion and configured for conveying fluid along the shaft, and at least one fluid outlet located at the distal end of the shaft and configured to direct fluid from the at least one fluid channel onto the optical component.

In any of these embodiments, the shaft may include a non-cylindrical outer surface defined by an outer surface of the first wall portion and an outer surface of the second wall portion.

In any of these embodiments, a width of the shaft in a first direction may be equal to an outer diameter of the first wall portion.

In any of these embodiments, the first wall portion may extend into the main body.

In any of these embodiments, a seal may be located in the main body for sealing against the first wall portion.

In any of these embodiments, the second wall portion may extend distally from the main body.

In any of these embodiments, the at least one fluid outlet may be formed by a distal end of the second wall portion.

In any of these embodiments, the shaft may include a single fluid channel and a single fluid outlet.

In any of these embodiments, the endoscope may be a sinuscope.

BRIEF DESCRIPTION OF THE DRAWINGS

Features will become apparent to those of ordinary skill in the art by describing in detail exemplary embodiments with reference to the attached drawings in which:

FIGS. 5A and 5B illustrate a fluid supply apparatus and tube set connector in which a liquid supply reservoir, for supplying the liquid for the scope cleaner, is incorporated into the connector, according to some embodiments;

DETAILED DESCRIPTION

Figure 1A:
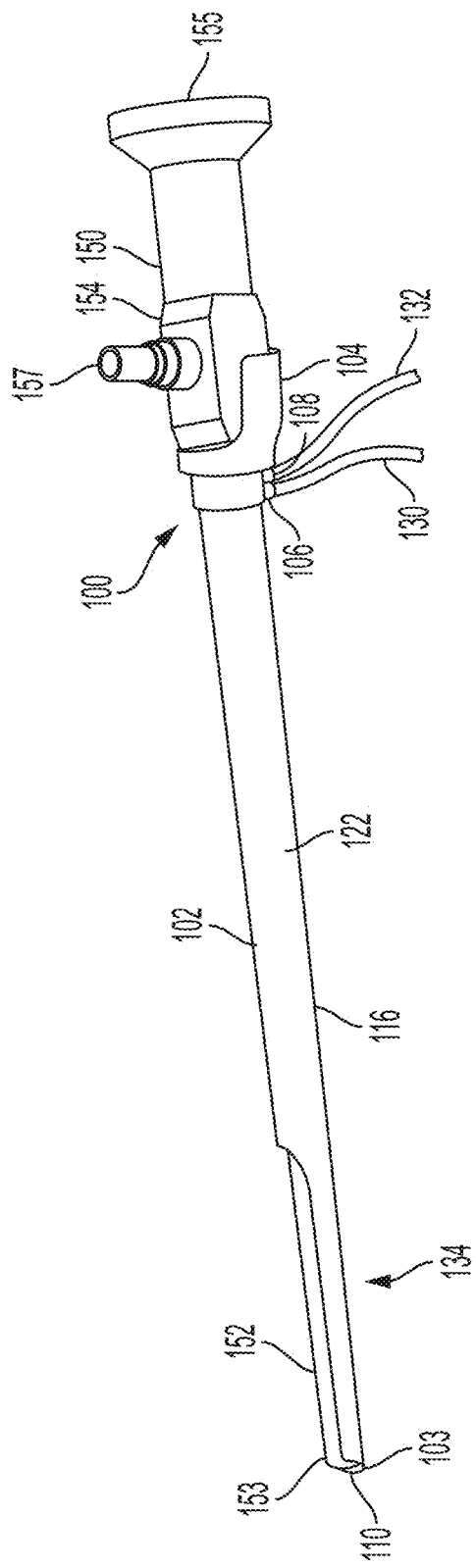
FIGS. 1A and 1B illustrate a surgical scope cleaner mounted on a surgical scope, according to some embodiments.

Reference will now be made in detail to implementations and embodiments of various aspects and variations of systems and methods described herein. Although several exemplary variations of the systems and methods are described herein, other variations of the systems and methods may include aspects of the systems and methods described herein combined in any suitable manner having combinations of all or some of the aspects described.

Described below are systems and methods, according to various embodiments, for cleaning a surgical scope during a surgical procedure with minimal interruption of the surgical procedure. According to some embodiments, a surgical scope cleaner includes a sheath that slides over the surgical scope and includes at least one nozzle for flushing the surface of the lens with a spray of a liquid such as saline and then blowing the lens with a burst of a gas such as carbon dioxide. Conduits running along the sheath lead from input ports at an end of the cleaner that can be connected to pressurized liquid and gas sources via a tube set. The sheath can be configured to slide over a standard size scope and to fit through the lumen of a standard size trocar. The surgical scope with mounted scope cleaner can be inserted through a trocar into the surgical cavity, and the cleaner can be used to clean the scope during the surgical procedure with minimal disruption to the procedure.

The at least one nozzle incorporated into the end of the sheath can point towards the lens of the scope to spray the cleaning liquid and blow gas with a high velocity directly at the lens. The at least one nozzle can be configured so that the high-velocity liquid spray clears off the entire surface of the lens—i.e., pressure washing the lens. The burst of gas can be provided after the liquid spray is complete to blow the surface of the lens dry and can also be provided at the same time as the liquid spray to enhance the liquid spray, increasing its velocity and hence its cleaning power. According to some embodiments, the sequence of the liquid spray and the gas burst, as well as the length of time they are activated, can be controlled by electromechanical valves in a fluid management system to which the scope cleaner is connected.

In some embodiments, the liquid and gas used for the scope cleaner are saline and carbon dioxide, which are used in most laparoscopic surgeries—the saline is often used to flush or irrigate when needed during surgery and carbon dioxide is often used to insufflate (or distend) the abdomen. Saline has been shown to be able to sufficiently clean blood, fat, and tissue debris from the lens of scopes used in surgery. Thus, surgical scope cleaning, according to some embodiments, can be incorporated into existing surgical systems.

According to some embodiments, a fluid management system to which the scope cleaner is connected can also be used to manage other fluids used in a surgical procedure. A fluid management system that provides, for example, carbon dioxide to the scope cleaner can also serve as an insufflator, providing the carbon dioxide to insufflate the surgical cavity. In some embodiments, the pressurized carbon dioxide gas that is received and regulated by the system for insufflation can also be used to pressurize the saline for the lens flushing and to blow the lens dry after the flushing cycle. Thus, scope cleaning can be provided without having to add an additional piece of equipment to the operating room.

According to some embodiments, the scope cleaner can be integrated into an insufflator tube set, which can help reduce clutter in the sterile field where the surgeon is operating. Clutter caused by the many hoses and wires that are attached to instruments in the sterile field and to control units and supply lines from outside the sterile field can restrict the movement of the surgical team during surgery as they try to avoid accidentally pulling or tripping on the hoses and wires and also increases the likelihood that an important instrument will be pulled onto the floor, causing damage and interruption to the surgical procedure. Thus, according to some embodiments, tubes, hoses, wires, etc., including those for the surgical scope cleaner, are combined into a single tube set, which reduces the clutter in and around the sterile field. A tube set that includes a scope cleaner can be disposable and single-use, or could also be reusable in order to reduce long-term costs to the user.

According to some embodiments, since the control of flow of the liquid and gas for the scope cleaner can be provided by a fluid management system, the surgical scope cleaning can be controlled by other equipment in the operating room through device control. The fluid management system can be connected to a control unit that can receive commands from surgical staff in several different ways and can transmit those commands to the fluid management system. These commands originate, for example, as voice commands, button presses on an endoscopic camera head for scrolling through menus and selecting options via the operating surgeon's display (OSD), button presses by the support staff outside of the sterile field on the touchscreen of the control unit, or on a touchscreen of a remote tablet that can be used with the control unit. According to some embodiments, the liquid and gas for scope cleaning can also be controlled by button presses on the touchscreen of the fluid management system itself.

In some embodiments, the control unit or other device can analyze video from the endoscopic camera connected to the surgical scope with scope cleaner to detect when the image becomes blurry due to scope smudging and/or scope fogging. Upon detecting scope smudging and/or fogging, the control unit can send a command to the fluid management system to initiate a cleaning sequence.

In the following description of the various embodiments, reference is made to the accompanying drawings, in which are shown, by way of illustration, specific embodiments that can be practiced. It is to be understood that other embodiments and examples can be practiced, and changes can be made without departing from the scope of the disclosure.

In addition, it is also to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some embodiments also relates to a device for performing the operations herein. This device may be specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each connected to a computer system bus.

Furthermore, the computers referred to in the specification may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

Figure 1B:
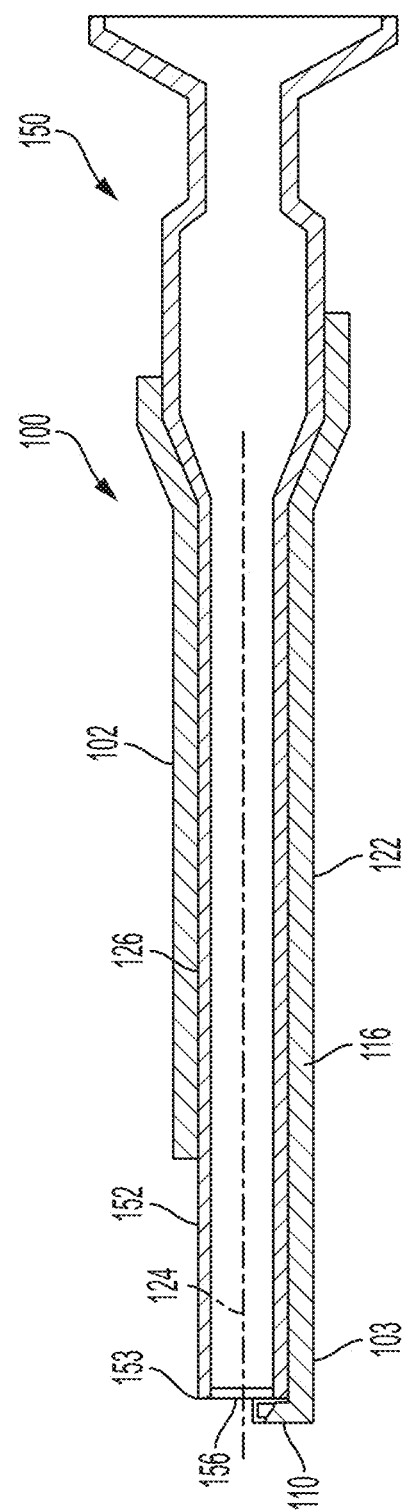

FIGS. 1A and 1B illustrate a surgical scope cleaner 100 mounted on a surgical scope 150, according to some embodiments. The surgical scope cleaner 100 can be configured for mounting on a standard size surgical scope and for insertion through the cannula of a standard size trocar into a surgical cavity. With the surgical scope cleaner 100 mounted, the surgical scope 150 can be used for imaging in the surgical cavity (along with an attached endoscope) during a surgical procedure. The surgical scope cleaner 100 can be used to remove smudging and/or condensation from the lens at the end of the surgical scope while the surgical scope remains in place in the surgical cavity during the surgical procedure.

In the illustrated embodiments, the surgical scope 150 includes an elongated and generally hollow tube 152 with a distal end 153 that is inserted into a body cavity, such as through the lumen of a trocar. The tube 152 extends from a housing 154 to which an eyepiece 155 is fitted to provide a viewing port through which the surgeon views the surgical field (for example, directly or through a connection between a viewing port, an endoscopic camera, and a display screen). A light port 157 extends from the housing 154 for connecting the scope 150 to an illuminator via a light cable to transmit light to a target via the scope 150. The surgical scope 150 can be, for example, a laparoscope. The surgical scope can be any type of surgical scope, including, for example, a surgical scope with an integrated camera.

The surgical scope cleaner 100 includes a sheath 102 that slides over the tube 152 of the surgical scope 150. The sheath 102 may define a generally cylindrical bore 126 that may be configured to fit to a tube of a standard size scope. The bore 126 may be sized so that the tube 152 can slide in and out of the sheath 102 while remaining radially fixed in position relative to the sheath 102 such the tube 152 and the bore 126 share substantially the same longitudinal axis 124.

A nozzle head 110 is located at a distal end 103 of the sheath 102 and extends past the distal end 153 of the tube 152 of the surgical scope 150. As explained further below, liquid and gas can be sprayed/blown from the nozzle head 110 to clean the lens at the end of the tube 152. The scope cleaner 100 is configured to remain mounted on the surgical scope as the surgical scope is being used throughout a surgical procedure. The lens can be cleaned as needed without the surgical scope needing to be removed from the surgical cavity.

The sheath 102 extends from a receiver 104 that is configured to receive a housing 154 of the surgical scope 150. The receiver 104 may include one or more retention features (not shown) for retaining the housing 154 of the surgical scope 150. In some embodiments, retention features may orient the scope with respect to the sheath 102, which may be important for the angular scopes (scopes having an angled distal end and a lens that points at an angle from the central axis of the scope, such as 30 or 45 degrees from the axis) in order to ensure that the nozzles are directed correctly at the angled lenses. In some embodiments, the receiver 104 may be shaped to receive the housing 154 in the correct angular orientation for ensuring that the nozzle head 110 is properly oriented with respect to an angled scope.

A liquid port 106 and a gas port 108 are provided in the receiver 104 and may be connected to a liquid supply line 130 and a gas supply line 132, respectively, that are connected to liquid and gas supplies. In some embodiments, the liquid and gas ports 106, 108 extend from the sheath 102. As described further below, liquid and gas supplied through the respective ports flows through at least one conduit in the sheath to at least one nozzle in the distal end 103 of the sheath 102 for spraying liquid and blowing gas onto the lens at the distal end 153 of the tube 152 of the surgical scope 150 to clean the lens of smudges and/or condensation.

Figure 1C:
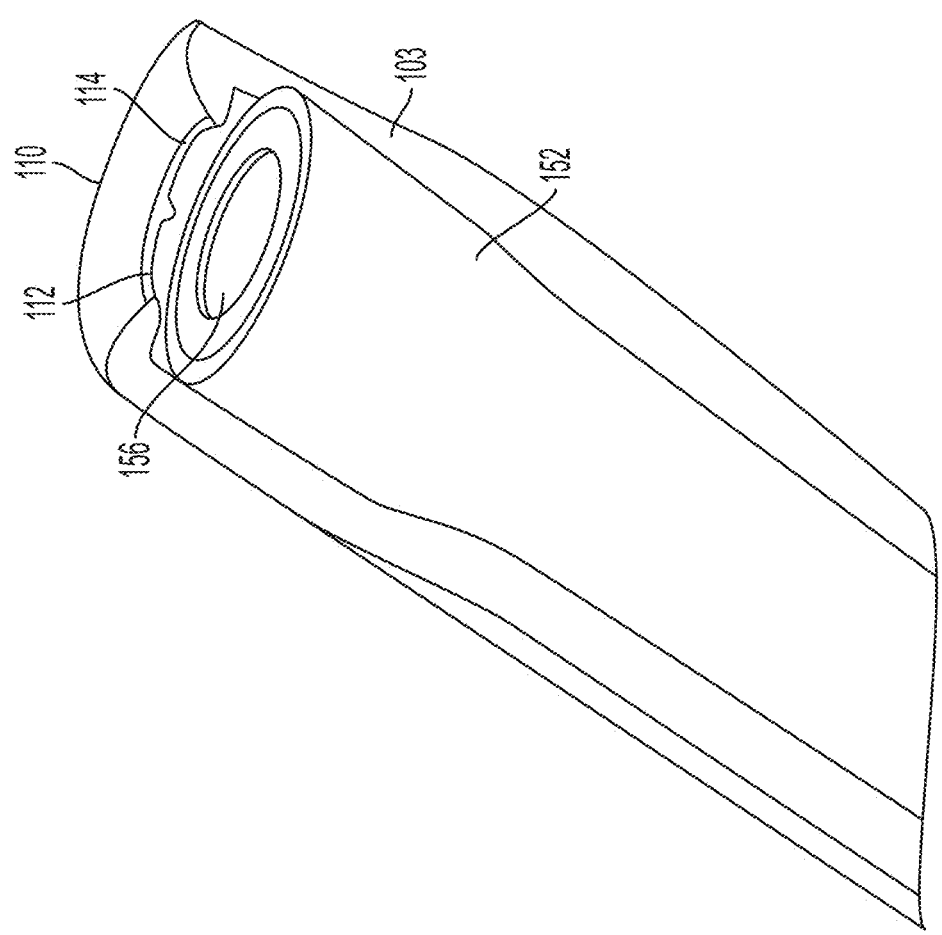
FIG. 1C illustrates the distal end of a scope cleaner mounted on a surgical scope, according to some embodiments.

FIG. 1C illustrates the distal end 103 of the sheath 102 with the distal end 153 of the tube 152 of the surgical scope 150 received therein. The distal end 103 has a nozzle head 110 that extends past the distal end 153 of the surgical scope 150. In the illustrated embodiment, the nozzle head 110 includes two nozzles located side-by-side—liquid nozzle 112 and gas nozzle 114. In other embodiments, the nozzles are spaced longitudinally, rather than circumferentially. The nozzles are configured to direct their respective flows onto the lens 156 at the distal end of the tube 152 of the surgical scope 150. In some embodiments, a single nozzle is provided and both the liquid and gas conduits feed into the single nozzle.

Figure 1D:
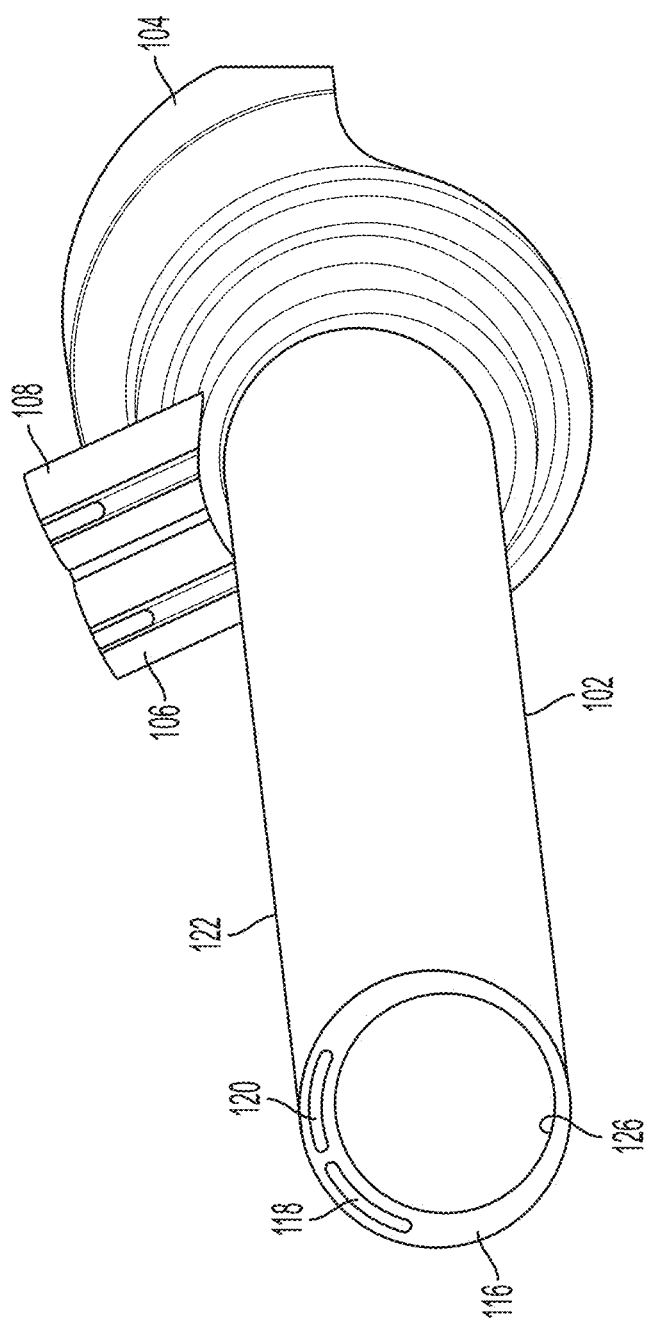
FIG. 1D is a cross-section of a sheath of a scope cleaner illustrating liquid and gas conduits, according to some embodiments.

FIG. 1D is a cross-section of the sheath 102 that illustrates the liquid conduit 118 and gas conduit 120 that extend longitudinally through the sheath 102 of the cleaner 100, according to some embodiments, to provide flow paths from the liquid and gas ports 106, 108 to the liquid and gas nozzles, 112, 114 at the distal end 103 of the sheath 102. The sheath 102 includes a wall 116, and the conduits 118, 120 are formed in the wall 116 such that the conduits are completely enclosed around their longitudinal perimeter. In the illustrated embodiment, the conduits 118, 120 are non-circular in cross-section and curve in a circumferential direction about the longitudinal axis 124 through a portion of the circumference of the wall. Curved conduits enable the outer diameter of the wall to be minimized while still providing a sufficient flow rate through the conduit. In other embodiments, the conduits may be circular or any other suitable shape depending on the wall thickness and the desired flow rate and pressure drop through the conduits. The conduits 118, 120 can extend longitudinally through the wall from the liquid and gas ports 106, 108 to the nozzle head 110. In some embodiments, the liquid and gas conduits merge prior to reaching the nozzle head such that a single conduit extends from a merging of the two conduits to the nozzle head 110. In some embodiments, the liquid and gas flow paths merge at or near the liquid and gas ports 106, 108 such that a single conduit extends substantially the entire longitudinal extent of the sheath 102.

The bore 126 of the sheath 102 may be cylindrical and may be configured to fit to a standard tube of a surgical scope. The outer surface 122 of the sheath 102 may also be cylindrical. In some embodiments, the outer surface 122 of the sheath 102 may extend about a longitudinal axis 125 that is different than the longitudinal axis 124 of the bore 126 of the sheath 102 (see FIG. 1E). This off-center arrangement results in one side of the wall 116 being thicker than the other size of the wall 116, with the thicker portion of the wall accommodating the conduits 118, 120. This is shown in FIG. 1D. Thus, the wall can accommodate the conduits while keeping the outer diameter of the sheath 102 to a minimum so that the sheath 102 can fit within a standard size trocar while being mounted on a standard size surgical scope.

Figure 1E:
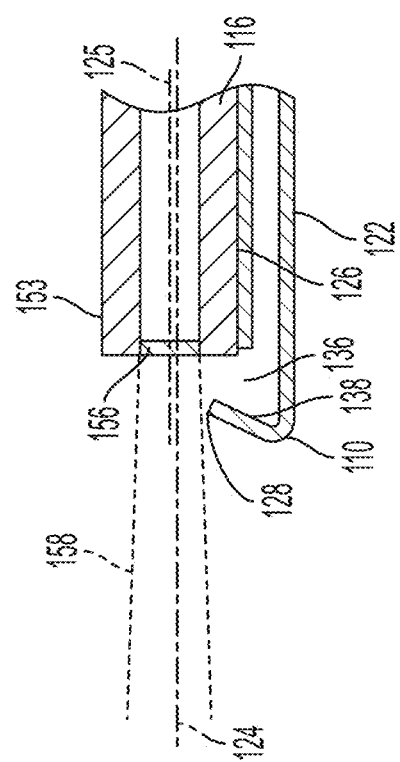
FIG. 1E is a cross-section of distal portions of a scope cleaner and surgical scope 150, according to some embodiments.

FIG. 1E is a cross-section of distal portions of the scope cleaner 100 and surgical scope 150. The distal end 153 of the tube 152 of the surgical scope 150 includes a lens 156. Each nozzle 112, 114 may be include a channel 136 in the nozzle head 110. A distal wall 138 of the channel 136 may be angled so that fluid moving longitudinally from the conduits 118, 120 is directed by the wall 138 toward the lens of the scope.

According to some embodiments, the nozzle head 110 is configured so that the field of view of the scope 150 is not obstructed by the scope cleaner 100. The field of view of the scope 150 is represented by dashed lines 158 in FIG. 1E. The nozzle head 110 may extend radially inward of the outer diameter 160 of the tube 152, but the radially innermost portion 128 of the nozzle head 110 may be positioned with respect to the longitudinal axis 124 of the tube 152 so that the innermost portion 128 does encroach into the field of view.

In some embodiments, the nozzle head 110 may be configured to reduce the amount of light that may be reflected onto the lens 156. For example, at least the portion of the nozzle head 110 that faces the lens 156 may be made from a light absorbing material and/or may be colored to absorb light (e.g., colored black).

Figure 1G:
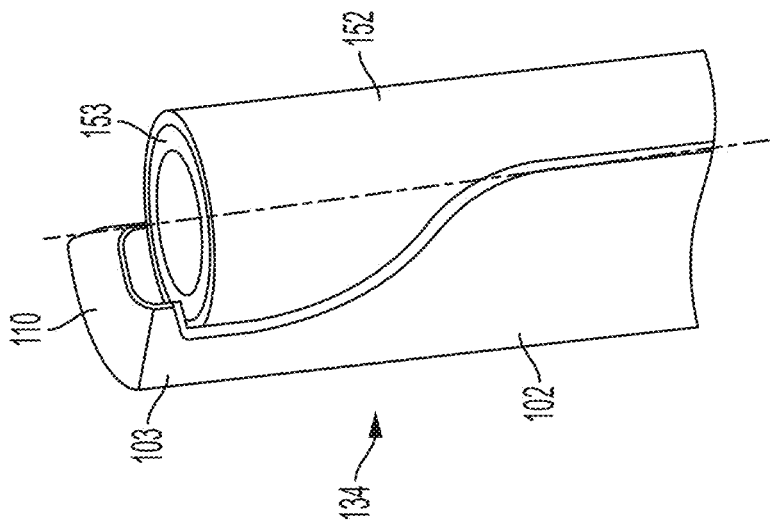
FIGS. 1F and 1G illustrate an alternative embodiment for locating the nozzle head outside of the field of view of the surgical scope, according to some embodiments.
Figure 1F:
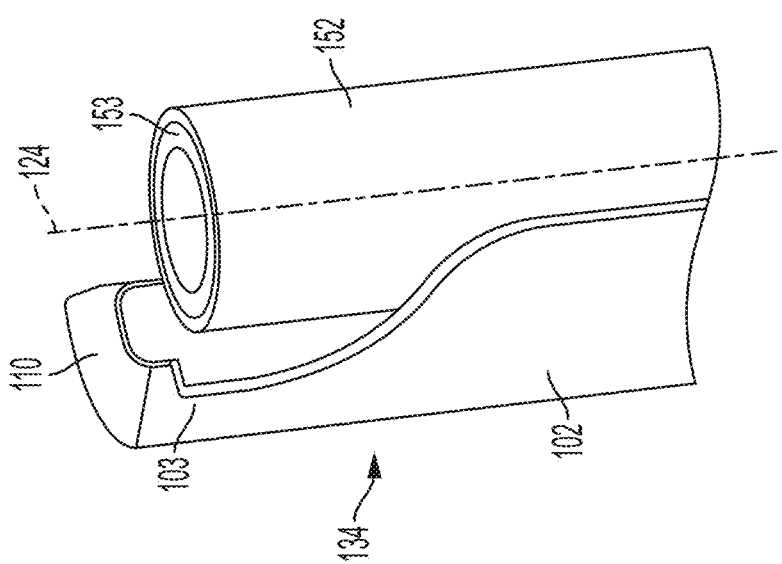

FIGS. 1F and 1G illustrate an alternative embodiment for locating the nozzle head 110 outside of the field of view of the surgical scope. In the illustrated embodiment, the distal portion 134 of the sheath 102 is angled away from the longitudinal axis 124 of the bore 126 of the sheath 102 so that the distal end 103 of the sheath 102 is spaced away from the distal end 153 of the tube 152 in the radial direction when the cleaner 100 is mounted to the scope 150. As a result, the nozzle head 110 is well outside of the field of view of the scope 150. The sheath 102 is configured so that the distal portion 134 can be bent back against the tube 152 so that the distal portion 134 can fit within a trocar when inserting the cleaner 100 into the surgical cavity, as shown in FIG. 1G. Once the distal portion 134 is through the trocar and into the surgical field, the distal portion springs back outward. In some embodiments, the compliance of the material that forms the sheath 102 enables the sheath to be elastically deformed inwardly toward the tube 152 and to then spring back outward to a repeatable position.

As shown in FIG. 1A, the distal portion 134 of the sheath 102 extends only partially around the tube 152 so that the distal portion of the sheath 102 can move inward and outward relative to the tube 152. In some embodiments, the proximal portion of the sheath 102 can extend fully around the tube 152 while the distal portion extends only partially around the tube 152. This enables the distal portion of the sheath 102 to angle away from the tube 152 while still allowing the sheath 102 to be securely mounted on the tube 152. In some embodiments, the sheath 102 extends only partially around the circumference of the tube 152 along the entire length of the tube 152. According to various embodiments, the length of the distal portion of the sheath 102 that extends only partially around the tube 152 is selected such that only the distal portion of the sheath—the portion that extends only partially around the tube 152—is located in a trocar during use. By having the portion of the sheath that is positioned in the trocar during use extend only partially around the tube 152, the overall size of the sheath with inserted tube 152 can be less such that a smaller trocar can be used as compared to a sheath that extends fully around the tube 152.

In embodiments in which the sheath 102 is configured to angle away from the tube 152, the nozzle head 110 may be made larger relative to embodiments in which the sheath 102 remains adjacent to the tube 152 along its entire length, which can increase manufacturability of the nozzle head 110 and/or increase nozzle performance.

Figure 1H:
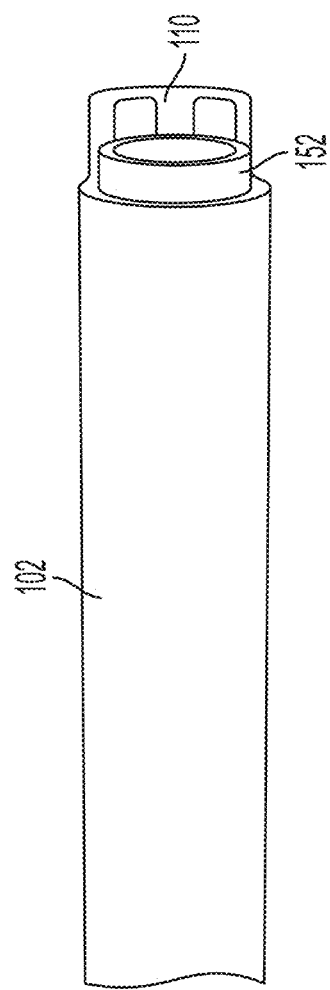
FIG. 1H illustrates an embodiment of a scope cleaner in which the sheath is not configured to angle away from the tube.

FIG. 1H illustrates an embodiment in which the sheath is not configured to angle away from the tube 152. In this embodiment, the sheath 102 can extend fully around the tube 152 the full length of the sheath 102. Embodiments in which the sheath 102 remains adjacent to the tube 152 along the full length of the sheath can also include a sheath that does not extend fully around the tube 152 for at least a portion of the length of the sheath.

In some embodiments, the scope cleaner 100 is made to be disposable and can be discarded after being used in a surgical procedure. In other embodiments, the scope cleaner may be configured for reuse and, as such, may be sterilizable. The scope cleaner 100 can be made of any suitable material, including any suitable plastic or metal. Examples of suitable plastics include Polycarbonate, Acrylic, Polyethylene terephthalate, Cyclic olefin copolymer, and Fluorinated Ethylene Propylene. In some embodiment, the scope cleaner is made via extrusion of one or more of these plastics or another suitable plastic. In some embodiments, the sheath 102 can be extruded out of a first plastic and the nozzle head 110 can be molded out of a different plastic and the two pieces bonded together. This might be desirable in embodiments in which the sheath 102 (in addition to the receiver 104 in some embodiments) has a first color and the nozzle head 110 has a second color, allowing for more material options for the extrusion and reduced costs and easier manufacturing. The scope cleaner can be molded, machined, 3D printed, or any combination thereof. The scope cleaner can be made of multiple components that are assembled together. For example, the nozzle head 110 may be affixed to the distal end 103 of a separate sheath 102 which may be attached to the receiver 104.

According to some embodiments, the surgical scope cleaner 100 can be connected to a liquid and gas supply system that controls delivery of liquid and gas to the surgical scope cleaner during use. As such, the surgical scope cleaner 100 can be free of any valving, which can provide greater simplicity and cheaper manufacturing, which may be especially advantageous for disposable scope cleaner embodiments. In other embodiments, the surgical scope cleaner can include one or more valves that may control flow of the liquid and/or gas. For example, the scope cleaner may include one or more push-button actuated valves that a user can actuate to provide the liquid spray and/or the burst of gas. One or more valves may be positioned, for example, in the receiver downstream of the ports 106, 108 or may be positioned upstream of the ports, such as in a tube set connecting the cleaner to the liquid and gas supplies.

Figure 1J:
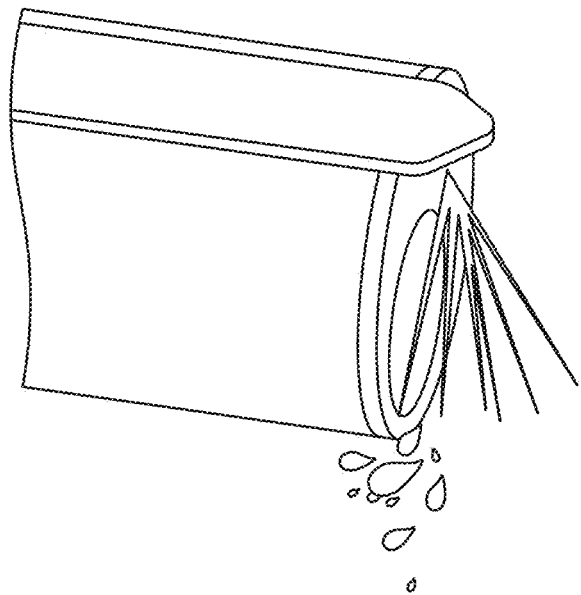
FIGS. 1I and 1J illustrate operation of a surgical scope cleaner, according to some embodiments.
Figure 1I:
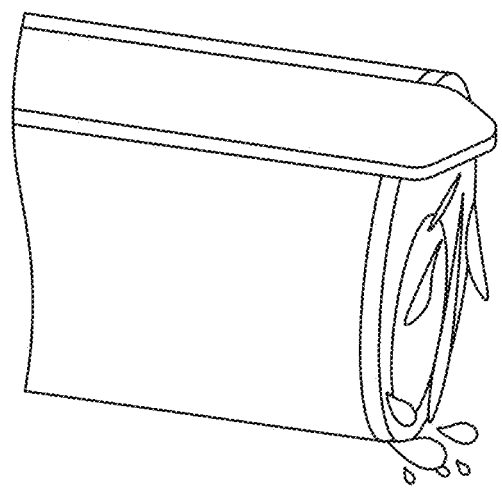

FIGS. 1I and 1J illustrate the operation of the surgical scope cleaner 100 according to some embodiments. First, as shown in FIG. 1H, liquid, such as saline, is sprayed from the nozzle head 110 onto the lens 156 to remove deposits on the lens. The deposits can be, for example, blood, fat, pieces of tissue, or bile from the surgical cavity, lubricant from the seals of the trocar through which the surgical scope was inserted, fluids sprayed in the surgical cavity during the surgical procedure, such as saline for flushing or therapeutic agents, or any other substance that may deposit on the lens. The liquid may be provided to the scope cleaner 100 from a pressurized source so that the liquid impacts the lens at a velocity that is sufficient to mechanically remove the deposits. The liquid may also serve to dissolve at least some of the deposits to aid in removal. In some embodiments, the liquid pressure at the pressurized source is at least 1 psi, at least 3 psi, at least 5 psi, or at least 10 psi. In some embodiments, the liquid pressure at the pressurized source is 50 psi or less, 30 psi or less, 20 psi or less, or 10 psi or less.

Next, as shown in FIG. 1J, a jet of gas is delivered from the nozzle head 110 onto the lens to remove the liquid and any loosened deposits remaining on the lens. The gas may be, for example, carbon dioxide, which is commonly available in the surgical field such as for insufflating the surgical cavity. As with the liquid, the gas may be provided from a pressurized gas source so that a burst of the gas is blown onto the nozzle with a relatively high velocity. In some embodiments, the gas pressure at the pressurized gas source is at least 5 psi, at least 10 psi, at least 50 psi, or at least 100 psi. In some embodiments, the gas pressure at the pressurized gas source is 500 psi or less, 250 psi or less, 150 psi or less, or 100 psi or less. The burst of the gas blows the sprayed liquid and any remaining deposits off of the lens, leaving the lens clean and clear. To the extent that some deposits remain, the cleaning sequence can be repeated as necessary.

In some embodiments, at least a portion of the period that the gas is delivered can overlap with at least a portion of the period of liquid spray. This can increase the velocity of the liquid spray, increasing its cleaning power.

Figure 2:
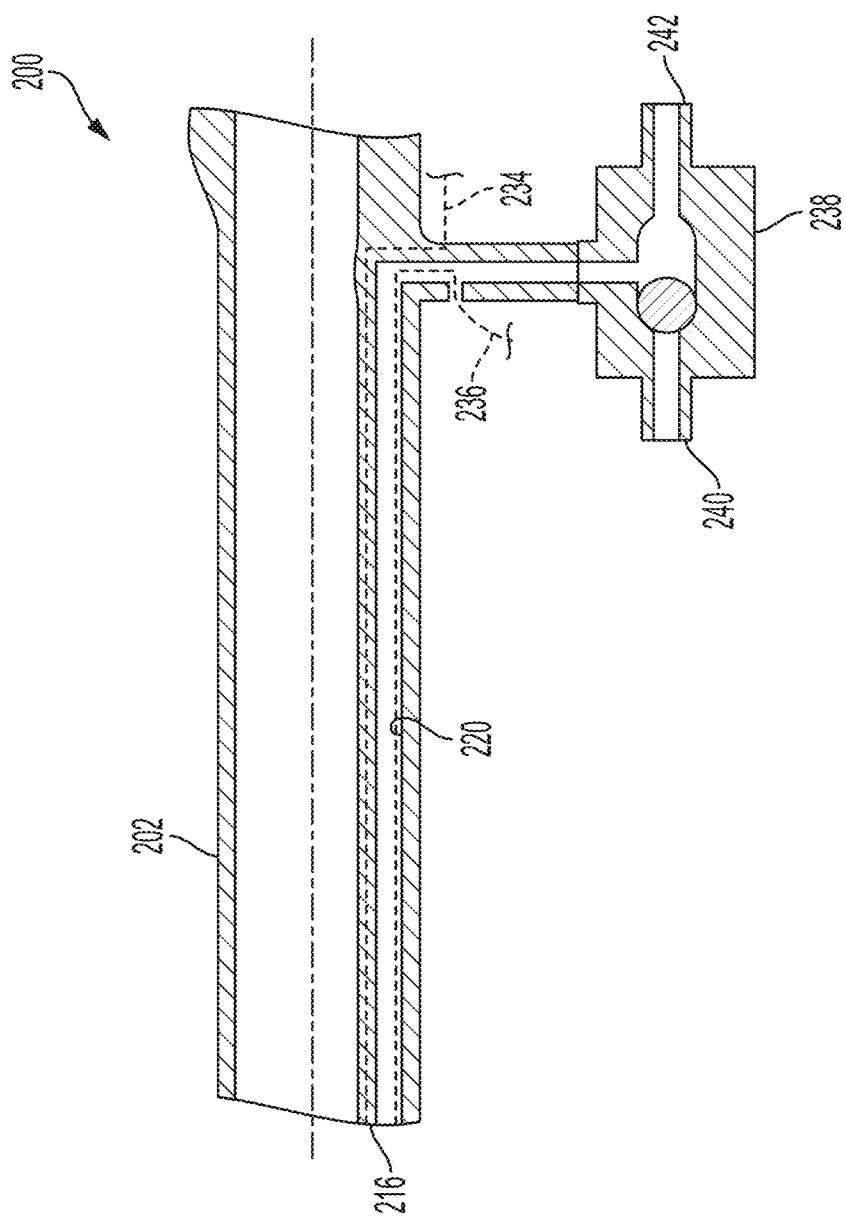
FIG. 2 is a cross section of a portion of a scope cleaner that is configured for warming and for providing a steady stream of gas to a surgical scope, according to some embodiments.

In some embodiments, the scope cleaner may be configured for preventing fogging of the lens of the scope by warming the surgical scope and/or providing a steady stream of gas to the surgical scope. FIG. 2 is a cross section of a portion of a scope cleaner 200 that is configured for warming and for providing a steady stream of gas to a surgical scope, according to some embodiments. One or more resistive heating wires 234 may be incorporated into the sheath 202 for warming to prevent fogging. One or more wires 234 can be molded into the wall 216 of the sheath 202 to warm the tube of a surgical scope received therein. Alternatively or additionally, one or more wires 236 can extend within the gas conduit 220 to warm the gas as it flows through. The one or more wires 234 and/or 236 can be connected to an electrical source via wiring that, for example, is incorporated into a tube set that includes tubes carrying liquid and gas for the scope cleaner 100.

In some embodiments, the scope cleaner 200 is configured for providing a steady stream of gas for preventing fogging while also providing a burst of gas for the cleaning sequence. The cleaner 200 may include a shuttle valve 238 that has two separate gas inlets 240 and 242 for connecting to two separate gas lines. A first gas inlet 240 can be used for providing low pressure gas that, when flowing, provides a steady stream of gas down the gas conduit 220 and out onto the lens of the scope. The low pressure gas could be regulated to be, for example, 2 psi or less. A burst of high pressure gas through the second gas inlet 242 will force the shuttle valve 244 to the position closing off the low pressure line, opening the flow path for the high pressure burst, which will flow down the gas conduit 220 to the lens of the scope. When the high pressure burst is finished, the pressure from the low pressure gas will shuttle the shuttle valve back to the position allowing the low pressure gas to flow.

In some embodiments, the low pressure gas flow can be the insufflating gas flow for insufflating the surgical cavity, which can eliminate the need for a separate insufflating line and insufflating inlet to the surgical cavity. In some embodiments, a scope cleaner is configured for scope heating, gas heating, and/or steady gas flow.

According to some embodiments, the liquid and gas supplies for the surgical scope cleaner can be incorporated into an apparatus that manages the flow of other fluids into and out of the surgical field. In addition to the liquid and gas supplies for the surgical scope cleaner, examples of other fluid management that can be provided, according to various embodiments, include providing insufflating gas for pressurizing the surgical cavity of a patient, evacuating smoke that may be created in the surgical cavity via cauterization, supplying irrigation liquid within the surgical cavity, removing liquid from the surgical cavity, and supplying of therapeutic agents to the surgical cavity.

Figure 3:
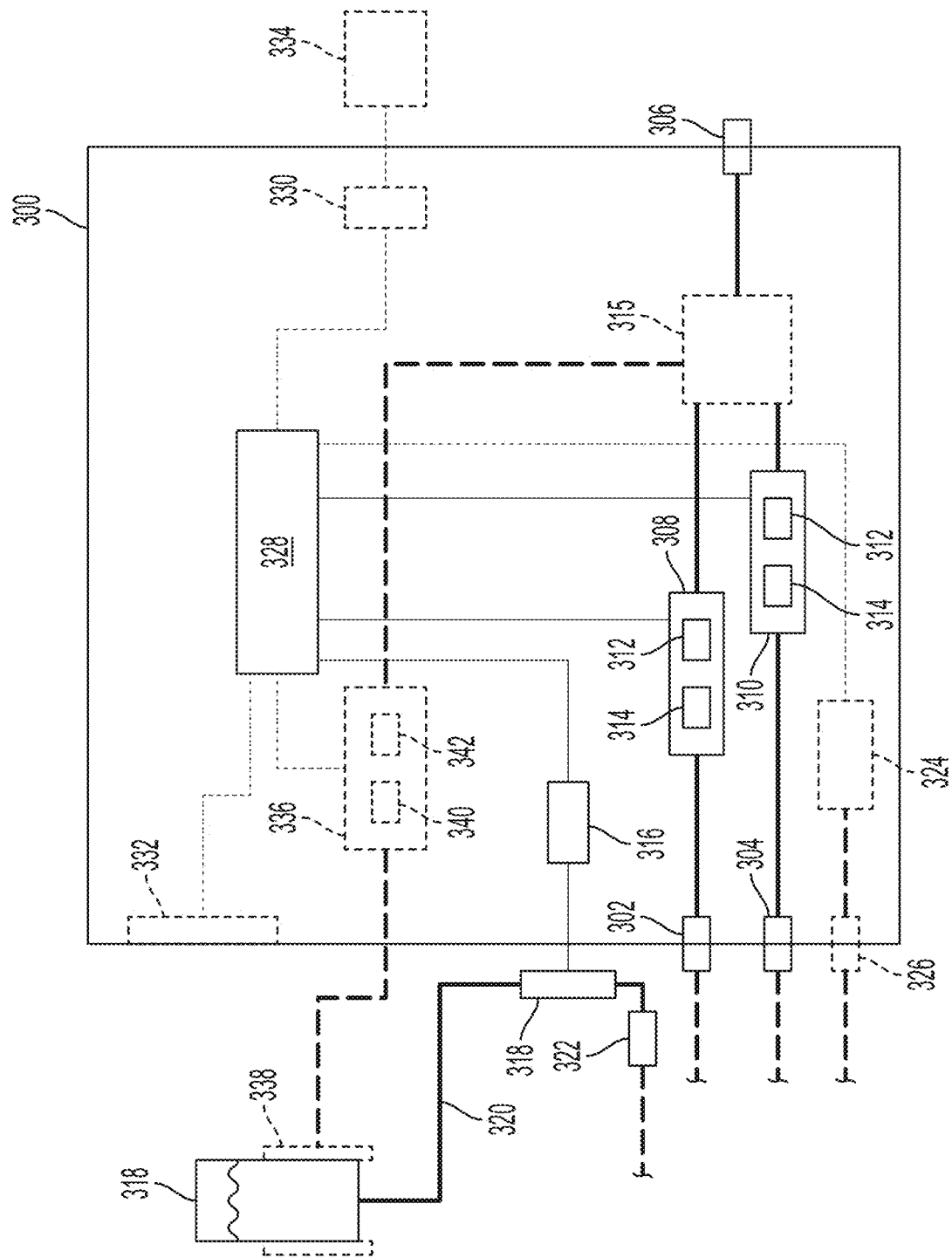
FIG. 3 is a block diagram of an apparatus for managing fluid flow into and out of a surgical field, according to some embodiments.

FIG. 3 is a block diagram of an apparatus 300 for managing fluid flow into and out of a surgical field, according to some embodiments. Apparatus 300 controls the flow of liquid and gas to a surgical scope cleaner, such as scope cleaner 100, and the flow of insufflating gas for pressurizing a surgical cavity. Apparatus 300 can be configured for managing the flow of any other fluids that are needed for the surgical field. A surgical scope cleaner and a device, such as a trocar, for directing insufflating gas into the surgical cavity can be connected to the apparatus 300 via, for example, flexible tubing that extends from the apparatus 300 into the surgical field.

Apparatus 300 includes a first gas supply port 302 for providing the gas supply to the surgical scope cleaner and a second gas supply port 304 for supplying an insufflating gas flow to the surgical cavity of a patient. The apparatus 300 includes a gas inlet port 306 for supplying gas to the apparatus 300. The gas inlet port 306 can be connected to a pressurized gas supply, such as a carbon dioxide wall or service head outlet or a carbon dioxide canister.

Gas supplies to the first and second gas supply ports 302, 304 can be controlled via first and second gas flow control subsystems 308 and 310, respectively. Each gas flow control subsystem can include, for example, a pressure regulator 312 for stepping down the pressure of the gas supplied to the apparatus 300 and a valve 314 for turning the flow of gas to the respective port 302, 304 on and off. In some embodiments, a single pressure regulator 315 may be used for both the first and second gas supply ports 302, 304.

Apparatus 300 also includes an actuator 316 for controlling flow of liquid to the surgical scope cleaner. The actuator 316 may be operatively connected to a flow device 318 that connects a liquid supply reservoir 320 to a liquid supply port 322. The surgical scope cleaner can be connected to the liquid supply port 322 via tubing for receiving liquid from the liquid supply reservoir 320 as controlled by the actuator 316 and flow device 318.

The actuator 316 and flow device 318 can be implemented in different ways according to various embodiments. In some embodiments, the flow device 318 is a valve that is moved between open and closed positions by the actuator 316. In other embodiments, the flow device 318 is a flexible tube that is compressed by the actuator 316 to close of the flow path through the flow device 318. The actuator 316 can be a linear actuator, such as a solenoid, that operates the valve or compresses the flexible tube. In other embodiments, the actuator 316 is a rotary actuator, such as a stepper motor or servomotor, that rotates the valve between open and closed positions. In some embodiments, the flow device 318 is a pump that is actuated by the actuator 316. The actuator 316 may be, for example, a motor that rotates a shaft onto which the pump is mounted.

In the illustrated embodiments, the flow device 318 is separate from and external to the apparatus 300, which results in the liquid flow path being entirely external to the apparatus 300. This arrangement can be advantageous in that there are no apparatus components that need sterilization. In other embodiments, the flow device 318 may be included in or otherwise as part of the apparatus 300.

The liquid supply reservoir 320 can be any suitable reservoir for providing the liquid needed for scope cleaning. For example, the liquid supply reservoir 320 can be a saline bag that is connected to the flow device 318 via tubing or can be combined with the flow device 318 into a single unit. In some embodiments, the liquid supply reservoir 320 is incorporated into the apparatus 300.

The apparatus 300 can include other fluid supply or discharge components. For example, the apparatus 300 can include a vacuum controller 324 for providing vacuum to the surgical field via a vacuum port 326. The vacuum can be used, for example, for evacuating smoke from the surgical field and/or suctioning liquid, such as blood, from the surgical field.

In some embodiments, the apparatus 300 includes a liquid reservoir pressurization subsystem 336 for pressurizing the liquid supply reservoir 320 using the same gas as used for the scope cleaning or a different gas. The pressurization subsystem 336 can provide pressurized gas, such as gas from the gas inlet port 306, to the liquid supply reservoir 320. In some embodiments, the pressurized gas can create head pressure in the reservoir 320. In other embodiments, the pressurized gas can compress the reservoir itself. For example, the reservoir may be a saline bag fitted within a pressurization sleeve 338 that receives the pressurized gas from the liquid reservoir pressurization subsystem 336.

The liquid reservoir pressurization subsystem 336 can include one or more valves 340 for controlling flow of pressurized gas, which can be the same gas as provided via the gas inlet port 306. In some embodiments, the liquid reservoir pressurization subsystem 336 can include a pressure regulator 342 for stepping down the pressure received via the inlet port 306 or via one or more upstream regulators, such as regulator 315. In some embodiments, the apparatus can be configured to control the liquid reservoir pressurization subsystem 336 to automatically depressurize the pressurization sleeve 338 at the end of a surgical procedure, such as when the insufflation is stopped.

The gas flow control subsystems 308, 310, the actuator 316, and any other electronic component of the apparatus 300 can be control via a controller 328. The controller 328 may include one or more processors and memory that stores instructions for execution by the one or more processors for controlling fluid management by the apparatus 300. The controller 328 may provide electrical signals to one or more valves and/or pressure regulators of the control subsystems 308, 310 and to actuator 316 actuating the actuator 316. The controller can also be used to control any other fluid management subsystems, including the vacuum controller 324 and the liquid reservoir pressurization subsystem 336.

The controller 328 may be communicatively connected to an external control system 334 via a communication port 330 for receiving liquid and gas supply control commands from the external system 334. For example, the controller 328 may receive a command to execute a cleaning sequence for the surgical scope cleaner, and in response, the controller may control the actuator 316 for supplying the liquid to the surgical scope cleaner for a predetermined period of time for spraying onto the lens of the surgical scope, as discussed above, and control the first gas flow control subsystem 308 for supplying a gas flow to the surgical scope cleaner for a second predetermined period of time for blowing liquid off of the lens of the surgical scope.

The apparatus 300 may include a user interface 332 for a user to control one or more aspects of the liquid and gas supply from the apparatus. The user interface 332 may be used, for example, for receiving commands for starting and stopping the insufflating gas flow and/or changing the insufflating gas pressure or for controlling any other function of the apparatus 300, according to various embodiments.

Figure 4A:
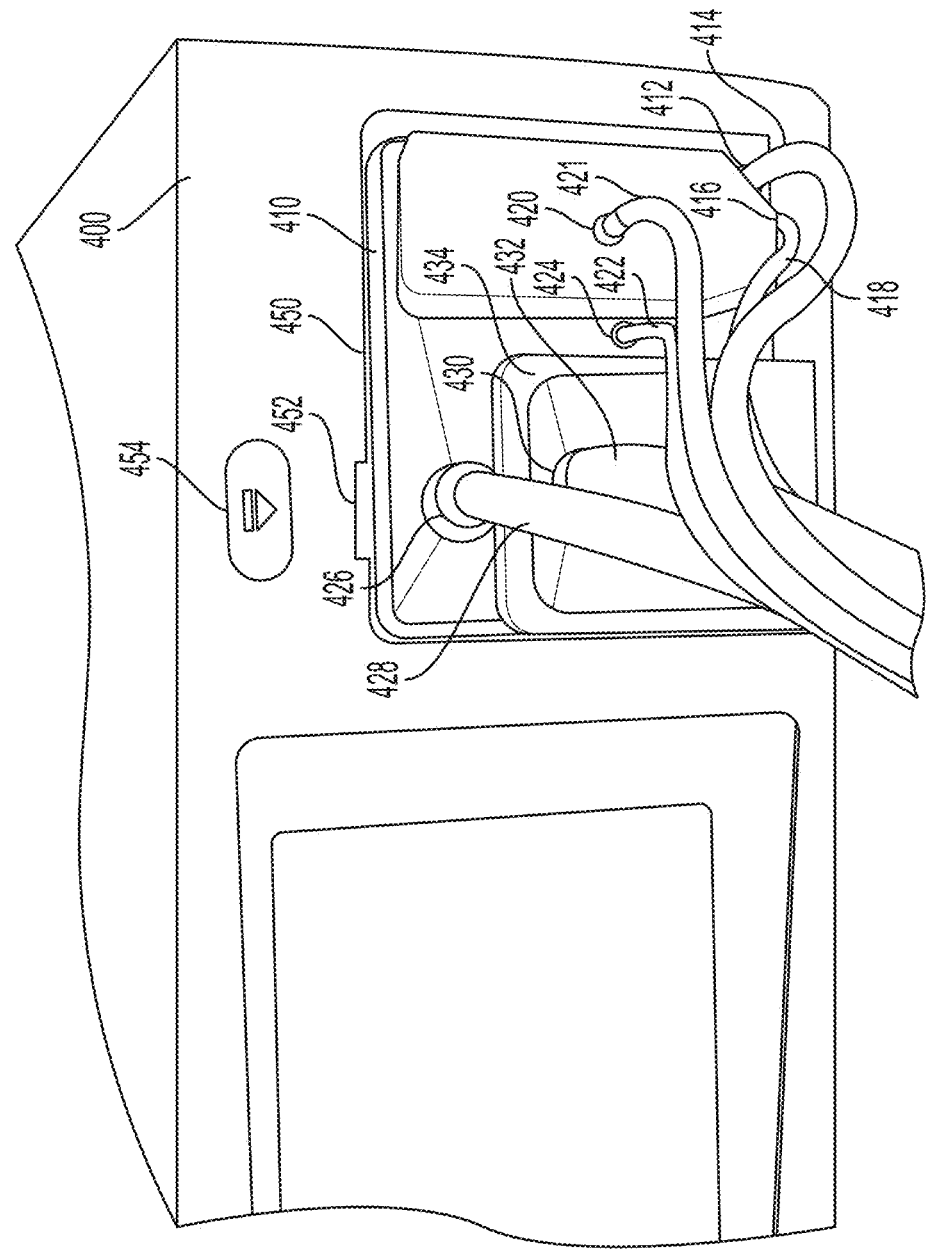
FIGS. 4A-4D illustrate a fluid supply apparatus and connector for connecting multiple fluid lines to the apparatus, according to some embodiments.

In some embodiments, lines for conducting fluids managed by a fluid supply apparatus, such as apparatus 300, to the surgical field are connected directly to the ports of the apparatus. In other embodiments, the supply lines are connected to a connector that is connected to a receptacle of the apparatus. FIG. 4A illustrates a fluid supply apparatus 400 in which a connector 410 is used to connect multiple fluid lines to the apparatus 400.

The connector 410 includes a gas supply port 412 for supplying gas to a surgical scope cleaner via a gas supply line 414, a liquid supply port 416 for supplying liquid to the surgical scope cleaner via a liquid supply line 418, and a liquid inlet port 420 for receiving liquid from an external liquid reservoir for the surgical scope cleaner via a liquid inlet line 421. A liquid reservoir pressurization port 424 can be included for supplying pressurized gas to a liquid supply reservoir, such as reservoir 320 of FIG. 3, via a liquid reservoir pressurization line 422.

The connector 410 also includes an insufflating gas supply port 426 for supplying an insufflating gas flow to the surgical cavity via an insufflating gas line 428 and a smoke evacuation port 430 for evacuating smoke from the surgical cavity via a smoke evacuation line 432. The connector 410 can include an inflow filter housing 434 that houses one or more filters for filtering smoke received via the evacuation port 430. The connector 410 can include other filters for filtering fluid provided to and received from the surgical field.

The connector 410 may be removably received in a receptacle 450 of the apparatus 300. One or more latches 452 may be used to retain the connector 410 in the receptacle 450. One or more ejection mechanisms 454 can be used to release the one or more latches 452 for removing the connector 410 from the receptacle 450.

Figure 4B:
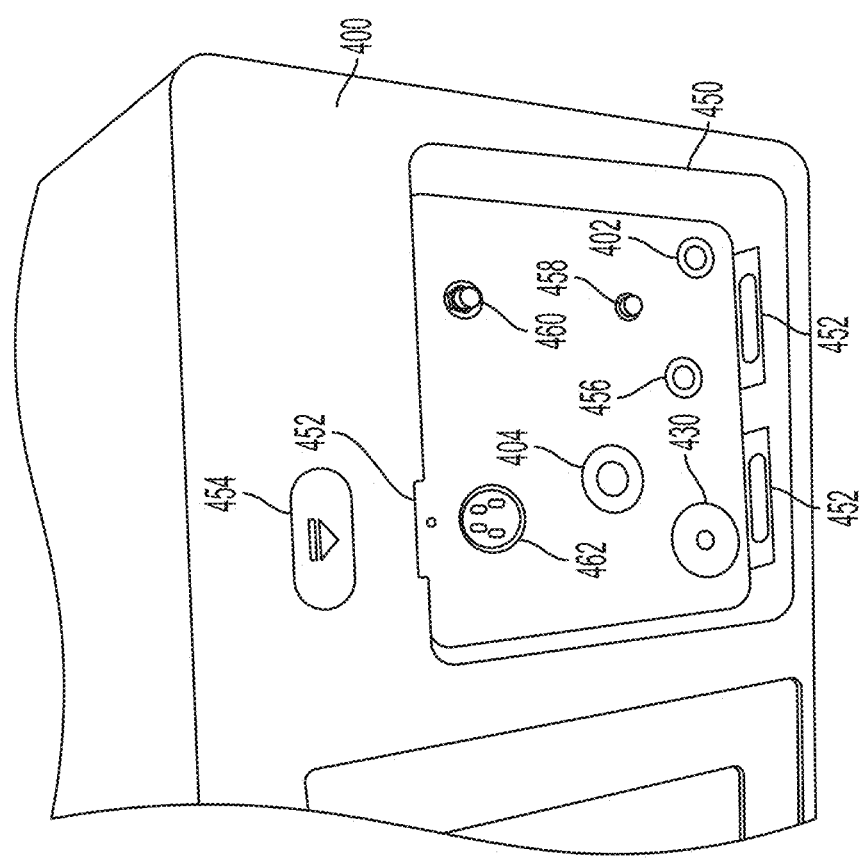

FIG. 4B illustrates the receptacle 450, according to some embodiments. The receptacle 450 includes the first gas supply port 402 for supplying gas flow to the surgical scope cleaner, a second gas supply port 404 for supplying insufflating gas flow to the surgical cavity, and a smoke evacuation port 430 for evacuating smoke from the surgical cavity. The receptacle 450 also includes a liquid reservoir pressurization port 456 for providing pressurization gas to a liquid supply reservoir, such as liquid supply reservoir 320 of FIG. 3.

The receptacle 450 may include a switch 458 that is depressed or otherwise actuated when the connector 410 is received in the receptacle 450. The switch 458 may be connected to a controller, such as controller 328 of FIG. 3, which may control the flow of one or more fluids based on the status of the switch so that there is no flow through one or more of the ports of the receptacle 450 when the connector 410 is not received in the receptacle 450. The receptacle 450 also includes an aperture 460 through which an end of an actuator for actuating a flow control device in the connector 410 extends, as discussed further below. The receptacle 450 may also include an electrical connection 462 for providing electricity to one or more heated tubes connected to the connector 410.

The rear side (not shown) of the connector 410 includes ports that fit to the ports of the receptacle 450 described above. One or more seals may be provided on any of the ports of the receptacle 450 and/or on any of the ports of the rear side of the connector 410. The rear side also includes an aperture for receiving the end of the actuator.

Figure 4C:
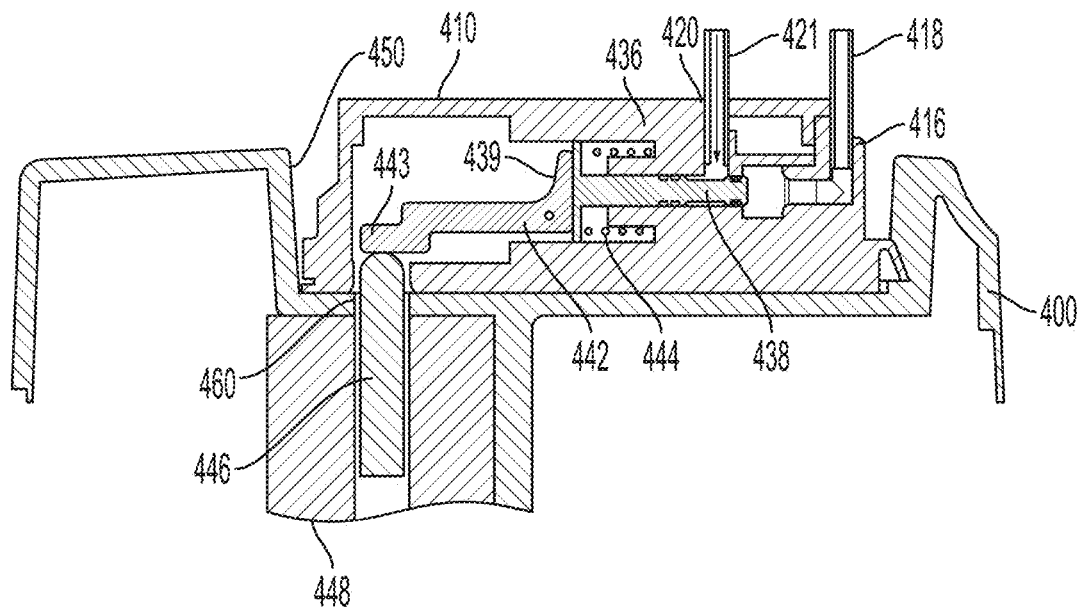
Figure 4D:
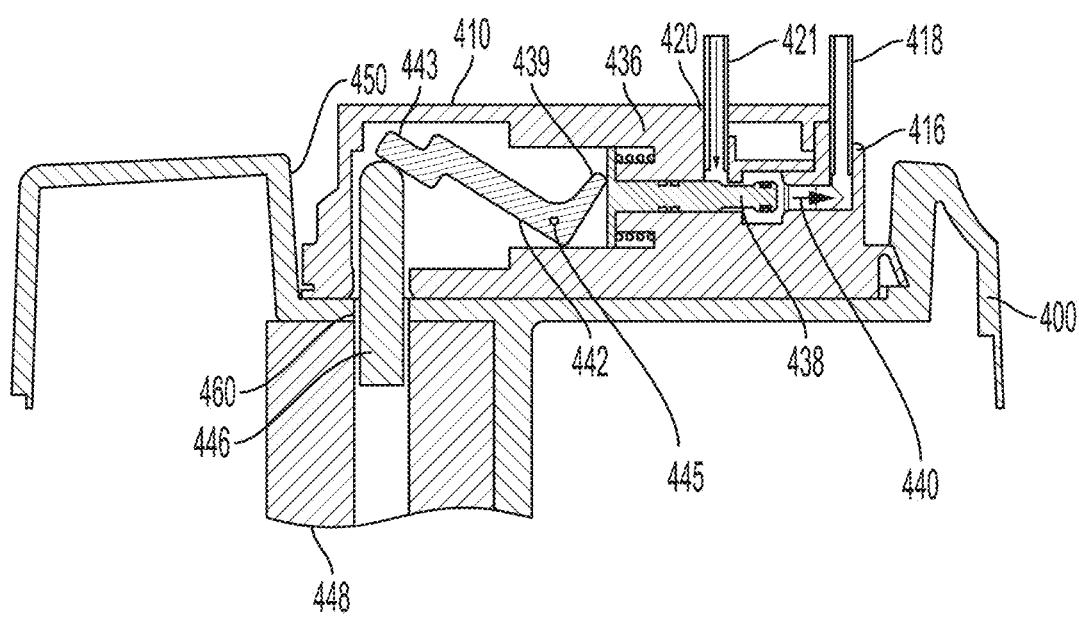

FIGS. 4C and 4D are cross sections of the connector 410 located in the receptacle 450, illustrating a flow device 436 incorporated into the connector 410. Flow device 436 includes a valve 438 that is moved laterally to open and close a liquid flow path 440 through the flow device 436. FIG. 4C illustrates the closed position and FIG. 4D illustrates the open position of the valve 438. The valve 438 is moved from the closed position to the open position by one end 439 of a lever 442 and is returned to the open position through the force of a spring 444. The lever 442 pivots about a pivot axis 445. To actuate the valve 438, a plunger 446 of a solenoid actuator 448 in the apparatus 400 pushes on the other end 443 of the lever 442, causing the lever to pivot about the pivot axis 445, pushing the end 439 of the lever 442 against the valve 438, forcing the valve to move laterally to the open position against the force of the spring 444. As shown in FIG. 4D, with the valve 438 in its open position liquid from a liquid supply reservoir can flow through the flow device 436 via the liquid inlet port 420 and out to the surgical scope cleaner via the liquid supply port 416.

Figure 5B:
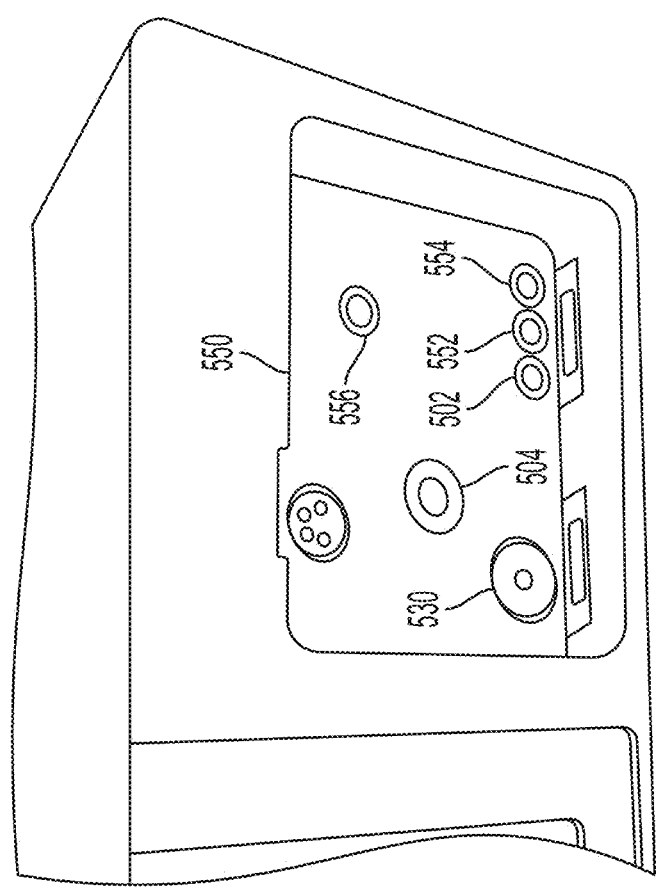

FIGS. 5A-5B illustrate a fluid supply apparatus 500 and tube set connector 510 in which a liquid supply reservoir for supplying the liquid for the scope cleaner is incorporated into the connector 510, according to some embodiments. Similarly to connector 410, connector 510, as shown in FIG. 5A, includes a gas supply port 512 for supplying gas to a surgical scope cleaner via a gas supply line 514, a liquid supply port 516 for supplying liquid to the surgical scope cleaner via a liquid supply line 518, an insufflating gas supply port 526 for supplying an insufflating gas flow to the surgical cavity via an insufflating gas line 528, and a smoke evacuation port 530 for evacuating smoke from the surgical cavity via a smoke evacuation line 532. However, unlike connector 410, connector 510 does not have a liquid supply port for receiving liquid from an external liquid reservoir. Instead, connector 510 includes a liquid reservoir 590 built in.

The connector 510 can include a reservoir filling port 592 for filling the liquid reservoir 590 with liquid, such as saline. The filling port 592 may have a one-way valve for sealing the port when the reservoir 590 is pressurized, as discussed further below. A bleeder valve 594 may be provided for bleeding air when filling the reservoir 590.

FIG. 5B illustrates the receptacle 550 of the apparatus 500 that receives the connector 510, according to some embodiments. The receptacle 550 includes the first gas supply port 502 for supplying gas flow to the surgical scope cleaner, a second gas supply port 504 for supplying insufflating gas flow to the surgical cavity, and a smoke evacuation port 530 for evacuating smoke from the surgical cavity. The receptacle 550 also includes a liquid reservoir pressurization port 556 for providing pressurized gas to the liquid reservoir 590 to pressurize the liquid provided to the scope cleaner.

According to some embodiments, a flow device in the form of a valve is provided within the apparatus 500 for controlling the flow of liquid from the reservoir 590. Accordingly, the receptacle 550 includes a liquid inlet 552 that receives liquid from the reservoir 590 (via a connection with an outlet on the back of the connector 510, which is not shown) and a liquid outlet 554 for providing the liquid to the scope cleaner via the connector 510. The flow device is provided in a flow line that extends between the liquid inlet 552 and outlet 554. The flow device is actuated by an actuator, such as a solenoid, so that the liquid flow can be turned on and off. Once the reservoir 590 is pressurized, opening the valve of the flow device allows liquid to flow to the scope cleaner.

Figure 6A:
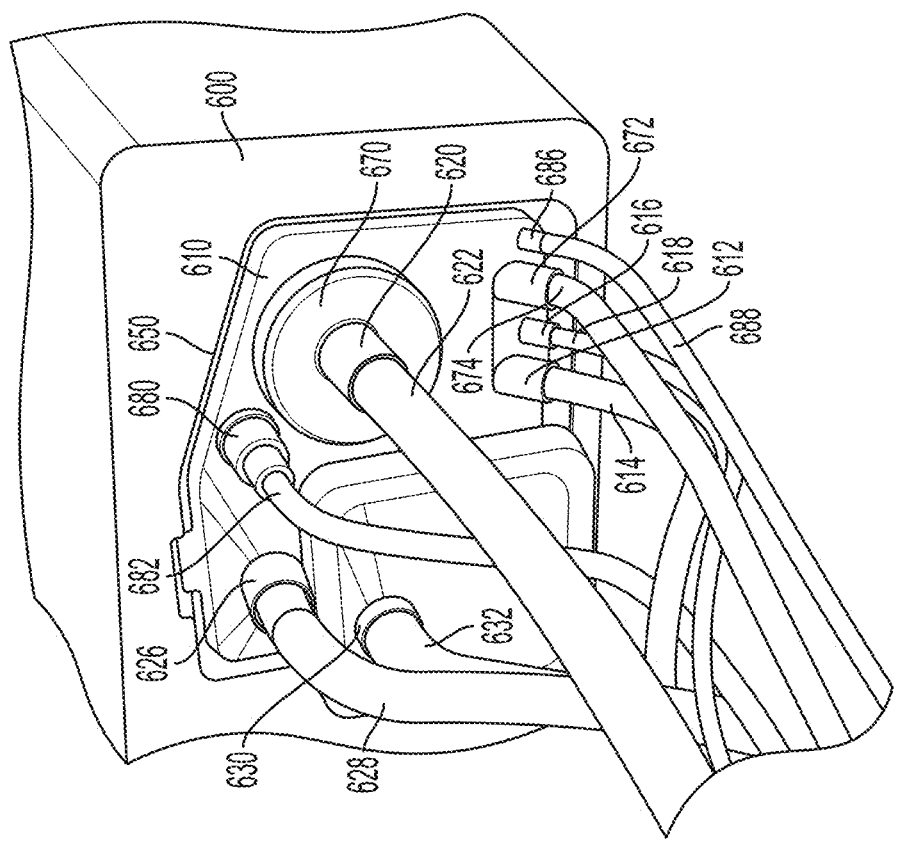
FIGS. 6A and 6B illustrate a fluid supply apparatus and tube set connector in which a pump is incorporated into the connector for pumping liquid from an external liquid supply reservoir to the scope cleaner, according to some embodiments.
Figure 6B:
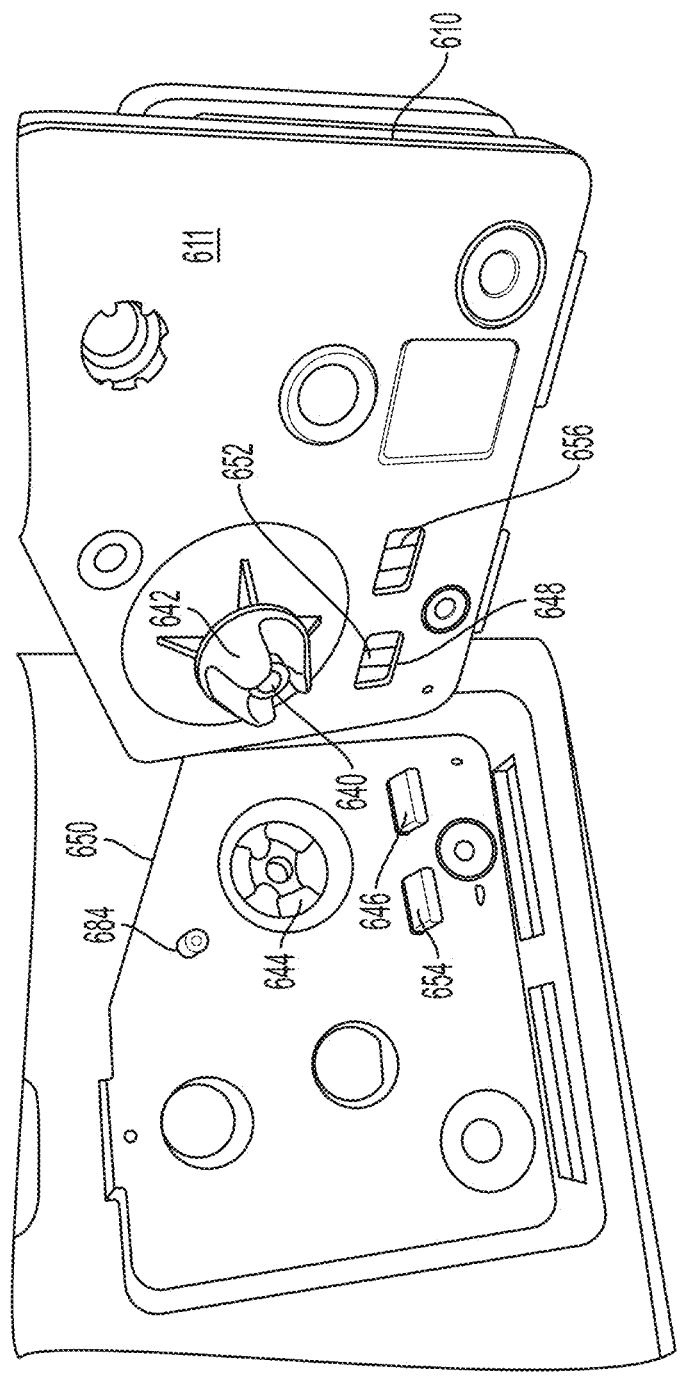

FIGS. 6A and 6B illustrate a fluid supply apparatus 600 and tube set connector 610 in which a pump is incorporated into the connector 610 for pumping liquid from an external liquid supply reservoir to the scope cleaner, according to some embodiments. The connector 610 includes a gas supply port 612 for supplying gas to a surgical scope cleaner via a gas supply line 614 and a liquid supply port 616 for supplying liquid to the surgical scope cleaner via a liquid supply line 618. A liquid inlet port 620 for receiving liquid from an external liquid reservoir, such as reservoir 320 of FIG. 3, via a liquid inlet tube 622 can lead into a pump impeller housed within a pump housing 670. The connector 610 also includes an insufflating gas supply port 626 for supplying an insufflating gas flow to the surgical cavity via an insufflating gas line 628 and a smoke evacuation port 630 for evacuating smoke from the surgical cavity via a smoke evacuation line 632.

FIG. 6B shows the receptacle 650 and the rear side 611 of the connector 610 that interfaces with the receptacle 650. Extending through the rear side 611 of connector 610 is a shaft 640 for a pump impeller housed within the connector 610. Mounted to the shaft 640 is a first coupler 642 that couples to and is driven by a second coupler 644 in the receptacle 650. The second coupler 644 is mounted to a shaft of a motor located within the apparatus 600. The motor drives the pump impeller to pump the liquid from the external liquid supply reservoir to the scope cleaner.

The pump can be started and stopped to control flow of liquid to the scope cleaner. Additionally or alternatively, an actuator can be used to open and close a liquid flow path in the connector 610. In the embodiment illustrated in FIG. 6B, a plunger 646 of the actuator, which can be in the form of a solenoid, extends from the receptacle 650 and is received in an aperture 648 in the rear side 611 of the connector 610. The plunger 646 extends to a liquid flow line 652 in the connector 610, which leads from the pump to the liquid supply port 616. The plunger 646 can be extended through action of the solenoid to pinch off the liquid flow line 652. Thus, in this embodiment, the flow device is the liquid flow line 652, which is pinched down by the plunger 646 of the actuator to shut off flow of the liquid. The pump can run continuously and flow of liquid to the scope cleaner can be controlled by the pinching of the liquid flow line 652. In some embodiments, the flow from the pump could also be controlled via a valve, such as valve 438 of FIGS. 4C-4D. In some embodiments, pump may be continuously pressurizing the liquid and flow can be controlled by, for example, a pinching actuator or a valve.

According to some embodiments, a pinching actuator can also be used for controlling flow of one or more other fluids, including, for example, the gas supply for the scope cleaner. FIG. 6B illustrates a second plunger 654 extending from the receptacle 650 for pinching a second flow line 656 in the connector 610. The second flow line can be, for example, a portion of the scope cleaner gas flow path through the connector 610. This arrangement can eliminate the need for a valve located in the apparatus for controlling the gas flow to the scope cleaner. In some embodiments, a valve is provided for controlling flow through second flow line 656.

According to some embodiments, including a pump in the connector 610 provides the ability for the apparatus to manage supply of liquid to the surgical field for additional purposes, such as for irrigation within the surgical cavity. One or more additional liquid flow path lines can lead from the pump to one or more additional tubes extending from the connector 610. Referring back to FIG. 6A, an irrigation outflow port 672 can be included for providing an irrigation outflow from the pump, via an irrigation tube 674, to an irrigation supply device used to irrigate the surgical cavity. In some embodiments, the second plunger 654 or an additional plunger, can be used to pinch a flow line for the irrigation liquid in the connector 610 for controlling the flow of the irrigation fluid.

According to some embodiments, a connector, such as connector 610, can include wires, cables, or other lines for providing electricity and/or data communication. In the embodiment illustrated in FIGS. 6A-6B, the connector 610 includes a monopolar RF connector 680 and cable 682 for providing electricity to an electrocautery instrument in the surgical field. The connector 680 can interface with a power port 684 in the receptacle 650, as shown in FIG. 6B. Connector 610 can also include a control signal connector 686 for connecting a control signal wire 688 that can be used to control one or more functions of the apparatus 600, such as the delivery of liquid and/or gas, the operation of the pump, or any other function. The wire 688 can lead, for example, to a switch or other remote control located in the surgical field that can be operated by a user.

According to some embodiments, an integrated tube set can be used to provide fluids managed by a fluid supply management apparatus, such as apparatus 300, 400, 500, or 600, to the surgical field. The integrated tube set can reduce the clutter in the surgical field by collecting fluid supply lines together. The integrated tube set can include a connector to which some or all of the lines are connected, such as any of connector 410, connector 510, or connector 610, which can simplify the set-up process for connecting the lines to one or more pieces of equipment. An integrated tube set can also include one or more integrated devices that can be used in the surgical field to deliver fluids to or from the surgical field, such as a surgical scope cleaner and a suction/irrigation device. Integrated tube sets can be disposable, single-use tube sets or can be reusable tube sets that are sterilized between each use.

Figure 7:
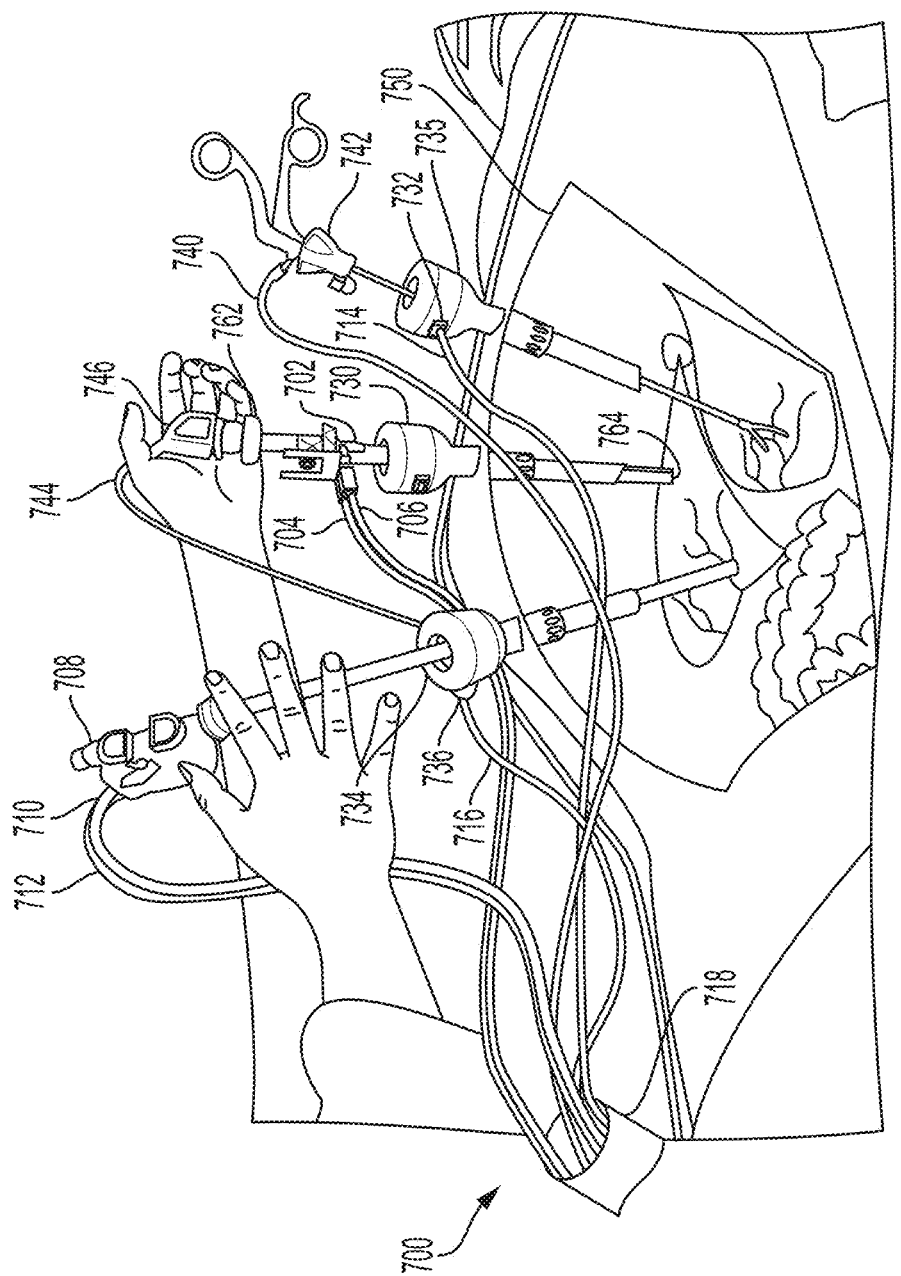
FIG. 7 illustrates the use of a tube set in a surgical field, according to some embodiments.

FIG. 7 illustrates the use of a tube set 700, according to some embodiments, in a surgical field. The tube set 700 includes surgical scope cleaner 702 configured in accordance with the principles discussed above, which is connected to a scope cleaning gas supply tube 704 and a scope cleaning liquid supply tube 706. In this embodiment, the surgical scope cleaner 702 is an integrated component of the tube set in which the scope cleaner and connected supply tubes are pre-connected, but in other embodiments, the scope cleaner is not provided as a part of the tube set, and the supply tubes 704 and 706 of the tube set are connected to a scope cleaner in preparation for a surgical procedure, such as in the operating room. The surgical scope cleaner 702 can be mounted to a surgical scope 762 fitted to an endoscopic camera 746. The surgical scope cleaner 702 and surgical scope 762 can be inserted into the surgical cavity 750 through a first trocar 730 for visualizing the surgical cavity. When the lens 764 at the end of the surgical scope 762 gets smudged or fogs, the scope cleaner 702 can be used to clean the lens 764 in accordance with the principles discussed above.

The tube set 700 can include a suction and irrigation device 708 that is connected to an irrigation supply tube 710 and a suction tube 712. The suction and irrigation device 708 can be inserted into a second trocar 734 for providing suction and irrigation in the surgical cavity 750. The suction and irrigation device 708 can be an integrated component of the tube set or can be connected to the tube set in preparation for a surgery.

The tube set 700 can also include an insufflation gas supply tube 714, which can be connected to a port 732 of a third trocar 735 for providing pressurized gas to the surgical cavity 750. The tube set also includes a patient outflow tube 716 that can be connected to a port 736 of the second trocar 734 for withdrawing gas, such as smoke, from the surgical cavity 750.

The tubes of the tube set 700 can be held together by an outer tube 718, which can help declutter the operating room. In some embodiments, the tubes are held together by one or more straps that are wrapped around the tubes. The tube set can include other lines that extend into the surgical field, such as a monopolar line 740 for providing current to a cauterization tool 742. The tube set could also include one or more data lines 744 and/or a light cable for connecting a camera control unit and/or an illuminator to an endoscopic camera 746 that is mounted to the surgical scope 762. Tube sets, according to various embodiments, can incorporate a laparoscopic sprayer that can convey pressurized gas from the fluid management apparatus to spray therapeutic agents inside the surgical cavity, such as hemostatic agents.

Figure 8A:
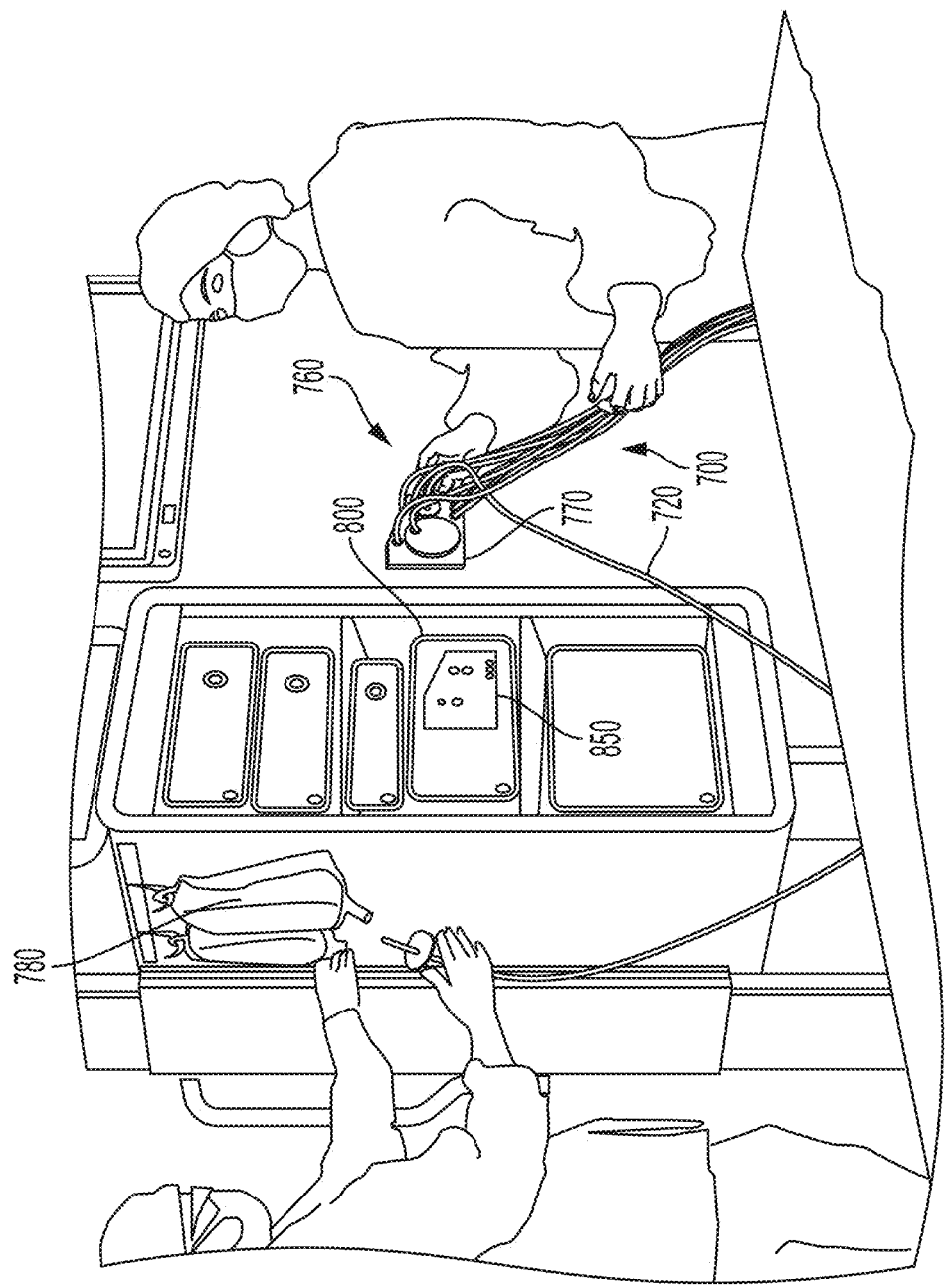
FIGS. 8A and 8B illustrate the connection of tube set to a fluid supply management apparatus, according to some embodiments.
Figure 8B:
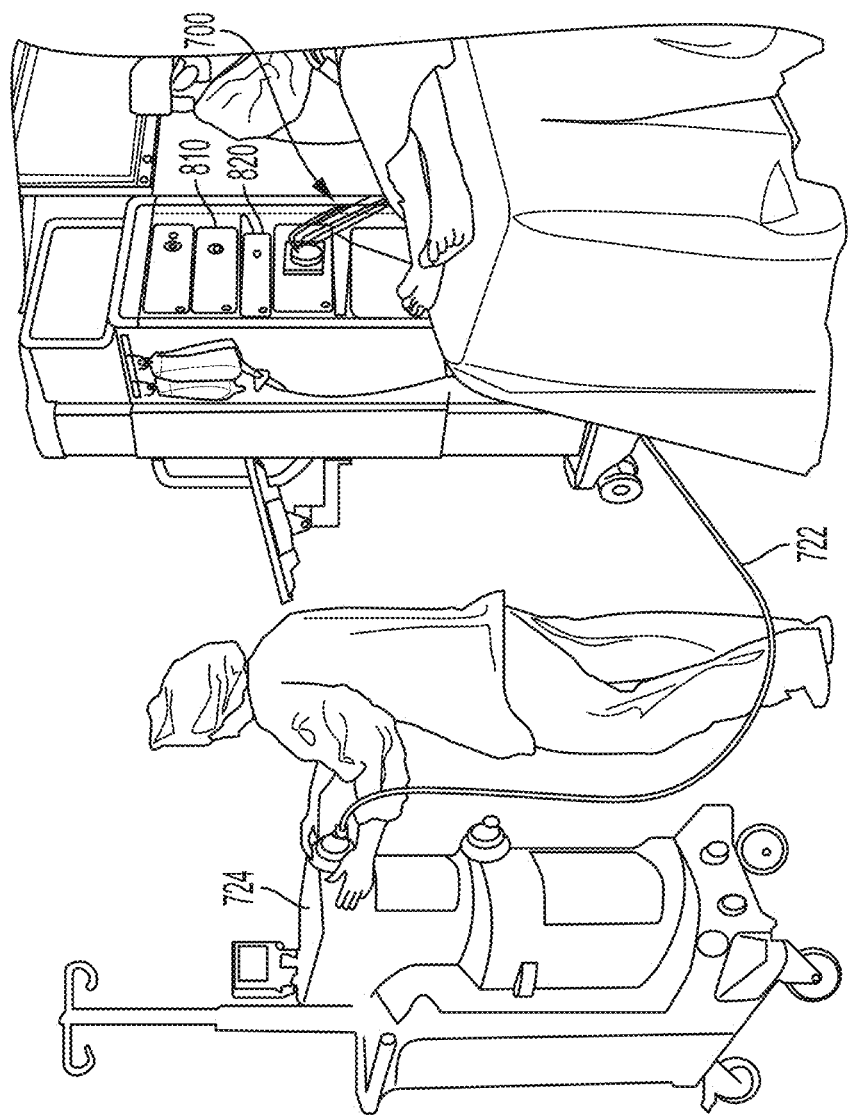

FIGS. 8A and 8B illustrate the connection of tube set 700 to a fluid supply management apparatus 800, such as any of apparatus 300, 400, 500, and 600 discussed above, according to some embodiments. The non-patient end 760 of the tube set 700 includes a connector 770, such as any of connectors 410, 510, and 610, to which some or all of the tubes of the tube set are pre-attached. The connector 770 is connected to the receptacle 850 of the fluid supply management apparatus 800. In the illustrated embodiment, the tube set 700 includes a liquid supply tube 720 that is connected to a liquid supply reservoir 780, which can be for example a saline bag, for supplying liquid to the surgical field, such as for the scope cleaner and/or irrigation supply device. FIG. 8B illustrates the connection of a suction line 722 of the tube set 700 to a suction apparatus 724.

Although not shown, one or more lines in the tube set can be connected to other equipment in the operating room. For example, one or more communication lines for an endoscopic camera can be connected to a camera control unit 810 and a light cable can be connected to an illuminator 820.

In some embodiments, a tube set can be configured so that the gas line connected to the scope cleaner can be disconnected from the scope cleaner and attached to another device used during the surgical procedure, such as a spraying wand to spray, for example, a hemostatic curing agent onto wound sites within the surgical cavity or medications to provide therapeutic healing effects to areas of the surgical cavity. The pressurized gas could be used to provide the power for a gas-driven instrument or power tool. In some embodiments, the liquid line connected to the scope cleaner can be disconnected from the scope cleaner for powering another device used in the surgical field. In some embodiments, both the gas and liquid lines could be disconnected from the scope cleaner and used for powering and/or controlling another device used in the surgical field. In some embodiments, a signal line from the fluid delivery system can be provided to connect to the device that the liquid and/or gas lines are connected to, whether the scope cleaner or any other device that interfaces with the liquid and/or gas lines. Information related to the type of device to which the line(s) are connected to the fluid delivery system can be communicated via this signal line so that the fluid delivery system can provide liquid and/or gas flows that are suitable for the connected device. For example, when the lines are connected to the scope cleaner, the fluid delivery system may register that the scope cleaner is connected (via the signal on the signal line) and may provide the liquid and gas flows per the cleaning sequence, and when the liquid and/or gas lines are connected to a device that is powered by the liquid and/or gas, the fluid delivery system may recognize this connected via the signal line and may provide the liquid and/or gas flows continuously.

Figure 9:
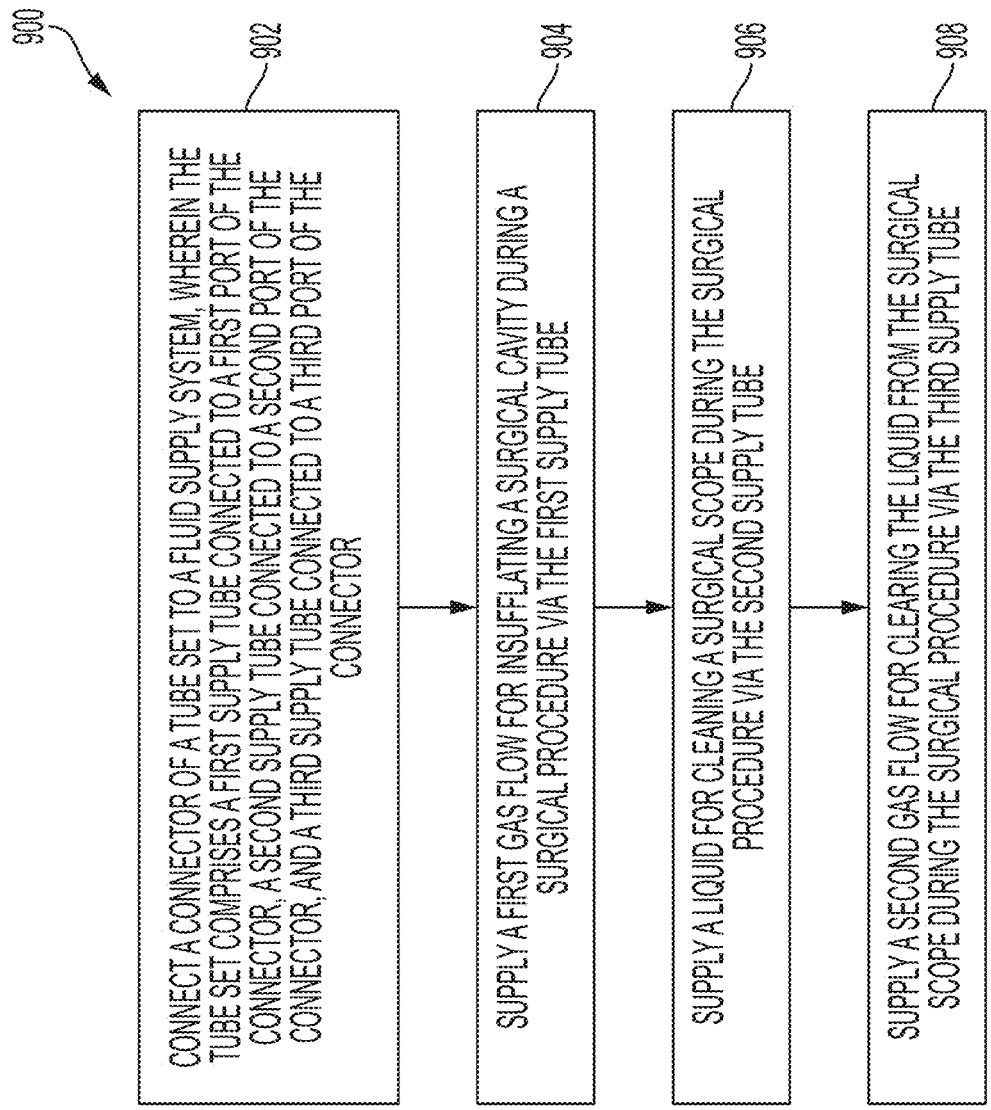
FIG. 9 illustrates a method for supplying fluid to a surgical field, according to some embodiments.

FIG. 9 illustrates a method 900 for supplying fluid to a surgical field, according to some embodiments. At step 902, a connector of a tube set is connected to a fluid supply system. The connector can be, for example, any of connectors 410, 510, or 610 and the fluid supply system can be any of apparatus 400, 500, or 600. The tube set can be, for example, tube set 700 of FIG. 7. The tube set includes a first supply tube connected to a first port of the connector, a second supply tube connected to a second port of the connector, and a third supply tube connected to a third port of the connector. For example, with reference to FIG. 4, the tube set can include insufflating gas line 428 connected to the insufflating gas supply port 426, liquid supply line 418 connected to the liquid supply port 416, and the gas supply line 414 connected to the gas supply port 412.

At step 904, a first gas flow for insufflating a surgical cavity is supplied during a surgical procedure via the first supply tube. For example, carbon dioxide can be supplied via the insufflating gas line 428 of FIG. 4 for insufflating the surgical cavity. At step 906, a liquid for cleaning a surgical scope is supplied during the surgical procedure via the second supply tube. For example, saline or a saline solution can be supplied via the liquid supply line 418 of FIG. 4 to a surgical scope cleaner, such as scope cleaner 100. At step 908, a second gas flow for clearing the liquid from the surgical scope is supplied during the surgical procedure via the third supply tube. For example, carbon dioxide can be supplied via the gas supply line 414 to the surgical scope cleaner.

In some embodiments, the method 900 further includes, prior to connecting the connector to the fluid supply system, unpackaging the tube set, which has been pre-sterilized and packaged. In some embodiments, the packaged tube set includes the scope cleaner. In other embodiments, the method 900 further includes attaching the second and third supply tubes that are connected to a surgical scope before or after the tube set connector is connected to the fluid supply system. In some embodiments, the method 900 includes discarding the tube set after use for a single surgical procedure. In other embodiments, the method 900 includes re-sterilizing the tube set after use.

In some embodiments, the method 900 further includes evacuating the surgical cavity via an evacuation tube connected to a fourth port of the connector. For example, smoke from the surgical cavity can be evacuated via a smoke evacuation line 432 connected to a smoke evacuation port 430 of connector 410 that is connected to apparatus 400.

Figure 10:
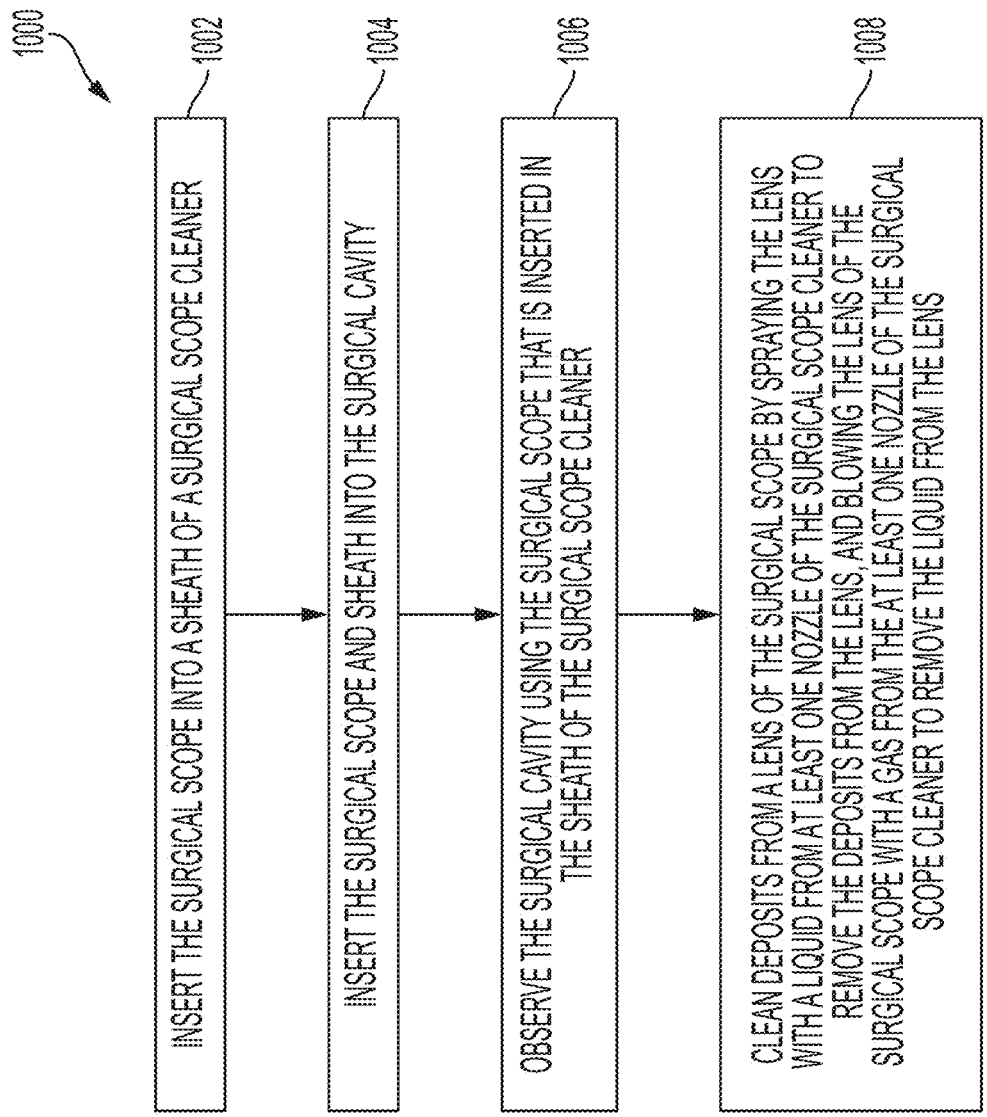
FIG. 10 illustrates a method for cleaning a surgical scope while the surgical scope is inserted in a surgical cavity, according to some embodiments.

FIG. 10 illustrates a method 1000 for cleaning a surgical scope while the surgical scope is inserted in a surgical cavity, according to some embodiments. At step 1002 the surgical scope, such as scope 150 of FIG. 1A is inserted into a sheath of a surgical scope cleaner, such as sheath 102 of scope cleaner 100. At step 1004, the surgical scope and sheath are inserted into the surgical cavity. For example, with reference to FIG. 1A and FIG. 7, the tube 152 of the surgical scope 150 with the mounted sheath 102 of the cleaner 100 are inserted through the lumen of a trocar 730 into the surgical cavity 750. At step 1006, the surgical cavity is observed using the surgical scope that is inserted in the sheath of the surgical scope cleaner. For example, images generated by endoscopic camera 746 of FIG. 7 can be displayed via a display in the operating room and observed by the surgeon.

At step 1008, deposits from a lens of the surgical scope may be cleaned by spraying the lens with a liquid from at least one nozzle of the surgical scope cleaner to remove the deposits from the lens, and blowing the lens of the surgical scope with a gas from the at least one nozzle of the surgical scope cleaner to remove the liquid from the lens. For example, with reference to FIG. 1C, deposits from lens 156 of the surgical scope 150 may be cleaned by spraying the lens 156 with saline from nozzle 112 of the surgical scope cleaner 100 to remove the deposits from the lens 156 and then blowing the lens 156 of the surgical scope 150 with a burst of carbon dioxide from nozzle 114 of the surgical scope cleaner 100 to remove the saline from the lens 156. Each of the liquid spray and the burst of gas can be provided for pre-determined periods of time that may be the same length or different lengths. The respective periods of liquid spray and burst of gas can overlap such that liquid and gas is provided simultaneously for at least a portion of the time.

In some embodiments, the cleaning sequence described above can be performed in response to a user command. For example, a user may see blurring on one or more endoscopic images or video displayed on the display in the operating room indicating smudging and/or fogging of the lens of the scope and may issue a command to commence the scope cleaning sequence. The command may be provided, for example, via a button press on the endoscopic camera, such as endoscopic camera 746 of FIG. 7. The button press can be communicated via communication line 744 to a camera controller, such as camera controller 810 of FIG. 8B. The camera controller can be communicatively connected to a fluid management apparatus. For example, with reference to FIG. 3, the camera controller can be a component of external system 334 or communicatively connected to external system 334, which is communicatively connected to fluid management apparatus 300. Based on the user's command, the external system 334 can send a command to the apparatus 300 to perform the cleaning sequence. The user could also push a button he/she temporarily attaches to the scope, the camera head, or that comes integrated into the proximal end of the scope cleaning sheath with an electrical wire running to the insufflator via the connector and said button/switch would be integrated into the tube set.

In some embodiments, an image analysis and control system, such as various embodiments of external system 334, includes image processing that analyzes one or more images or one or more video frames generated by the endoscopic imager to detect scope smudging and/or fogging. Once the scope smudging and/or fogging has been detected, the control system may send a control command to the fluid management apparatus 300 to perform a cleaning sequence. Accordingly, in some embodiments, the control system includes one or more processors and memory storing one or more programs for performing a method to automatically detect deposits on a lens of a surgical scope and send a command to a connected apparatus to initiate a cleaning sequence for the surgical scope. An exemplary method performed by a control system, according to various embodiments, is method 1200 of FIG. 12. At step 1202 of method 1200, the control system receives one or more images of a surgical field from an endoscopic imager that is communicatively connected to the control system. The endoscopic imager includes an endoscopic camera connected to a scope, such as surgical scope 150, that is inserted in the surgical cavity. The scope may be received in a scope cleaner, such as surgical scope cleaner 100, or may have integrated cleaning functionality, such as scope 1100 of FIGS. 11A-E. At step 1204, the control system automatically detects a deposit on a lens of the surgical scope by analyzing the one or more images. Any suitable image processing algorithm or combination of algorithms may be used to detect deposits. At step 1206, the control system sends a command to a communicatively connected fluid management apparatus to provide one or more fluids to the surgical field for cleaning the surgical scope. In some embodiments, the command may be sent automatically in response to detecting deposits. According to various embodiments, in response in response to receiving the command from the control system, the fluid management apparatus supplies a liquid flow and/or a gas flow from the apparatus to the surgical scope cleaner or surgical scope with integrated cleaning for cleaning a lens of the surgical scope during a surgical procedure. In some embodiments, the liquid flow is supplied first for a first period and the gas flow is supplied for a second period that is at least partially subsequent to the first period.

In some embodiments, the image analysis and control system may provide a notification to the user, such as on a display in the operating room, that smudging and/or fogging has been detected. The image analysis and control system may wait for a confirmation from the user to initiate the cleaning sequence. The user may confirm that the cleaning sequence may be performed via any suitable user input, such as a voice command, a button press on the camera head, or a button press on a user interface of the image analysis and control system. In response to receiving the user command, the image analysis and control system may send an initiate cleaning sequence command to the fluid management apparatus, which may respond by controlling the cleaning sequence.

The fluid cleaning apparatus may control a cleaning sequence by actuating the actuator to provide flow of the liquid to the scope cleaner. For example, the controller 328 of apparatus 300 may send a command to actuator 316 to cause the flow device 318 to permit the flow of liquid received from the reservoir 318. With reference to FIGS. 4C and 4D, this may include controlling the solenoid 448 so that the plunger 446 moves the lever 442 to cause the valve 438 to move to the open position. In some embodiments, the cleaning sequence includes spraying the lens with liquid for a first predetermined period. Once this period has elapsed, the actuator may be controlled to stop the flow of liquid. For example, the plunger 446 may be retracted and the valve 438 may return to a closed position due to the force of the spring 444.

The fluid cleaning apparatus may continue the cleaning sequence by opening a valve for pressurized gas to flow to the surgical scope cleaner. For example, with reference to FIG. 3, the controller 328 may control the valve 314 to open, allowing pressurized gas from gas supply inlet 306 to flow (as regulated by, for example, regulator 312 or regulator 315) to the scope cleaner. The gas may be provided for a second predefined period of time. The burst of gas may be provided while the liquid is being provided or may be provided entirely after the liquid is provided.

According to some embodiments, surgical scope cleaning is built into the surgical scope itself by building at least one fluid channel and at least one fluid outlet into the scope shaft. This can be particularly advantageous for small surgical scopes, such as sinuscopes, for which a separate cleaning sheath may be prohibitively large for inserting into narrow passageways, such as in the sinuses. Thus, according to various embodiments, the scope and cleaning sheath functions are combined into a single solution—a scope having integrated cleaning capability. By combining these two conventionally separate functions, the overall size of the scope with cleaning capability can be minimized and a much smaller cross-sectional area can be achieved than a separate scope and sheath solution. According to various embodiments, integration of the cleaning solution into the scope has other advantages, including reducing the amount of reflections and other visual impairments (obstruction of view, etc.) that are introduced by a separate sheath and maintaining the working length of the scope, which would otherwise be shortened by a sheath.

A scope with integrated cleaning, according to various embodiments, can be particularly suitable for functional endoscopic sinus surgery (FESS) and Transnasal Skull Base surgeries for which the cross-sectional size of the inserted device is a major design limiter due to the limited size of the operating space. According to various embodiments, by integrating the cleaning channel into the scope, the size of the combined solution can be as small as an elliptical cross section with a height of 4.6 mm and width of 4.0 mm (which is the size of a conventional sinuscope) while maintaining a cleaning channel cross-section that is sufficiently large for use with pumps and tubing that are conventionally used in the operating room.

FIGS. 11A-E illustrate a scope having integrated cleaning functionality, according to some embodiments. Looking first at FIG. 11A, scope 1100 includes a shaft 1102 that extends distally from a main body and is configured for insertion into a surgical cavity during use. The shaft 1102 includes at least one fluid channel (described further below) that directs fluid to at least one fluid outlet 1114 at the distal end 1116 of the shaft 1102. The at least one fluid outlet 1114 is configured to direct fluid onto an optical component 1112 (such as a window or lens) located at the distal end 1116 of the shaft.

The main body 1104 includes an eyepiece 1106 located at a proximal end 1118 of the scope 1100. The eyepiece 1106 can be configured for connecting the scope 1100 to an imager. The main body includes a light port 1108, which can be configured as a light cable connector for connecting to a light cable that provides illumination to the scope 1100. The main body 1104 also includes at least one fluid port 1110 for connecting to at least one fluid supply and/or exhaust supply system for supplying fluid and/or exhaust to the scope 1100. The at least one fluid port 1110 can be configured for a liquid, such as saline, or for a gas, such as carbon dioxide (as used herein, the term "fluid" encompasses liquids and gases). In some embodiments, the main body 1104 includes a single fluid port 1110. In some embodiments, the main body 1104 includes multiple fluid ports 1110, such as a liquid port and a gas port. In some embodiments, a fluid port 1110 can be used to supply both a liquid and a gas, either sequentially (such as via upstream valving) or simultaneously (such as to increase the pressure of supplied liquid.) In some embodiments, fluid flows both into and out of the port 1110, such as due to a peristaltic operation of a fluid supply system. The at least one fluid port 1110 can be configured for connecting to conventional tubing used for supplying fluids to the surgical field.

Figure 11A:
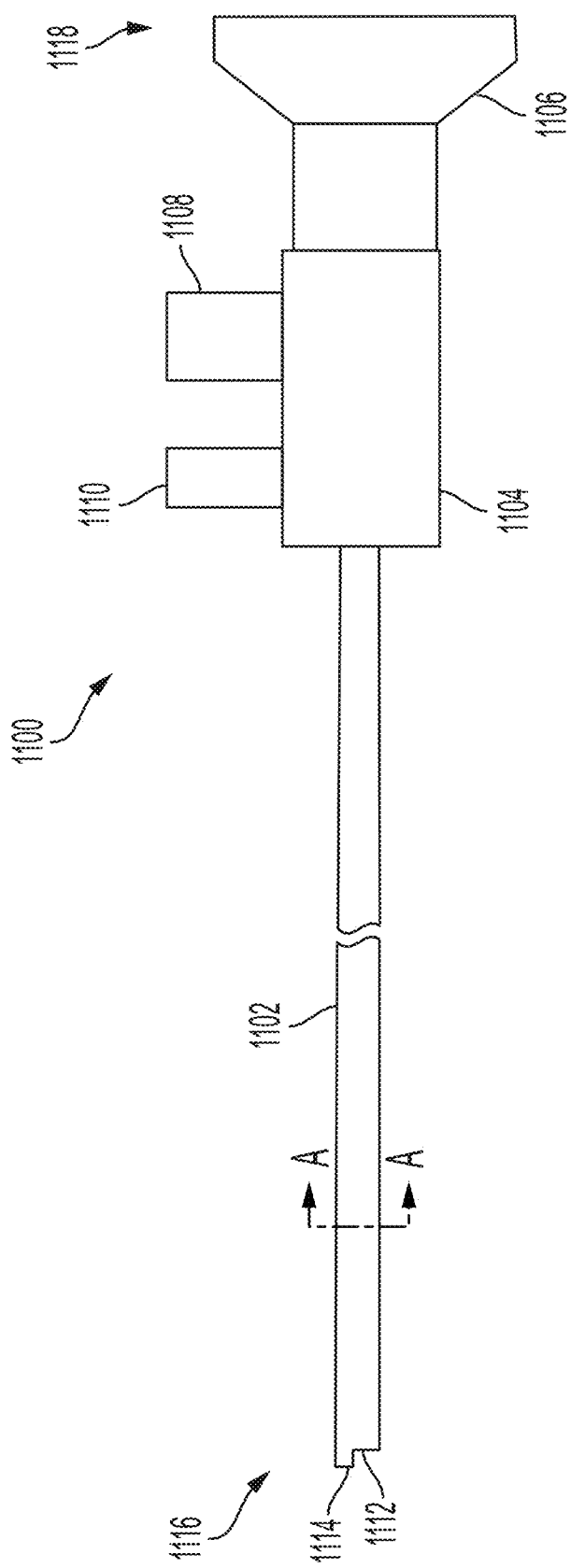
FIG. 11A illustrates an scope with integrated cleaning, according to some embodiments.
Figure 11B:
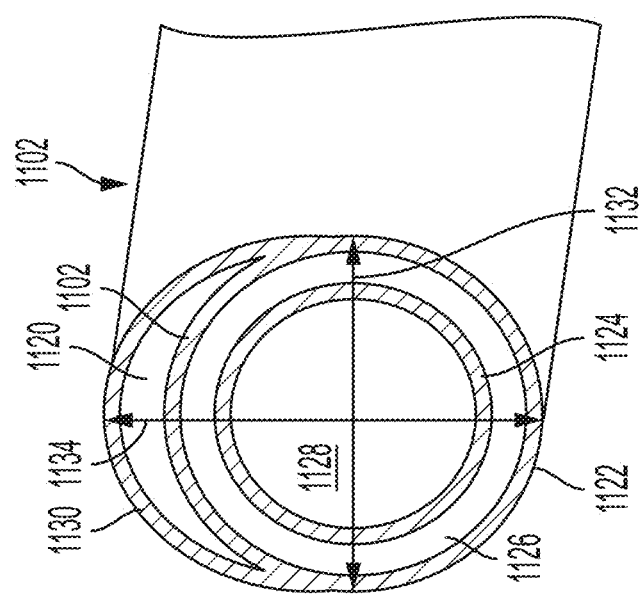
FIG. 11B illustrates a perspective view of a cross-section of a portion of a shaft of a scope with integrated cleaning, according to some embodiments.
Figure 12:
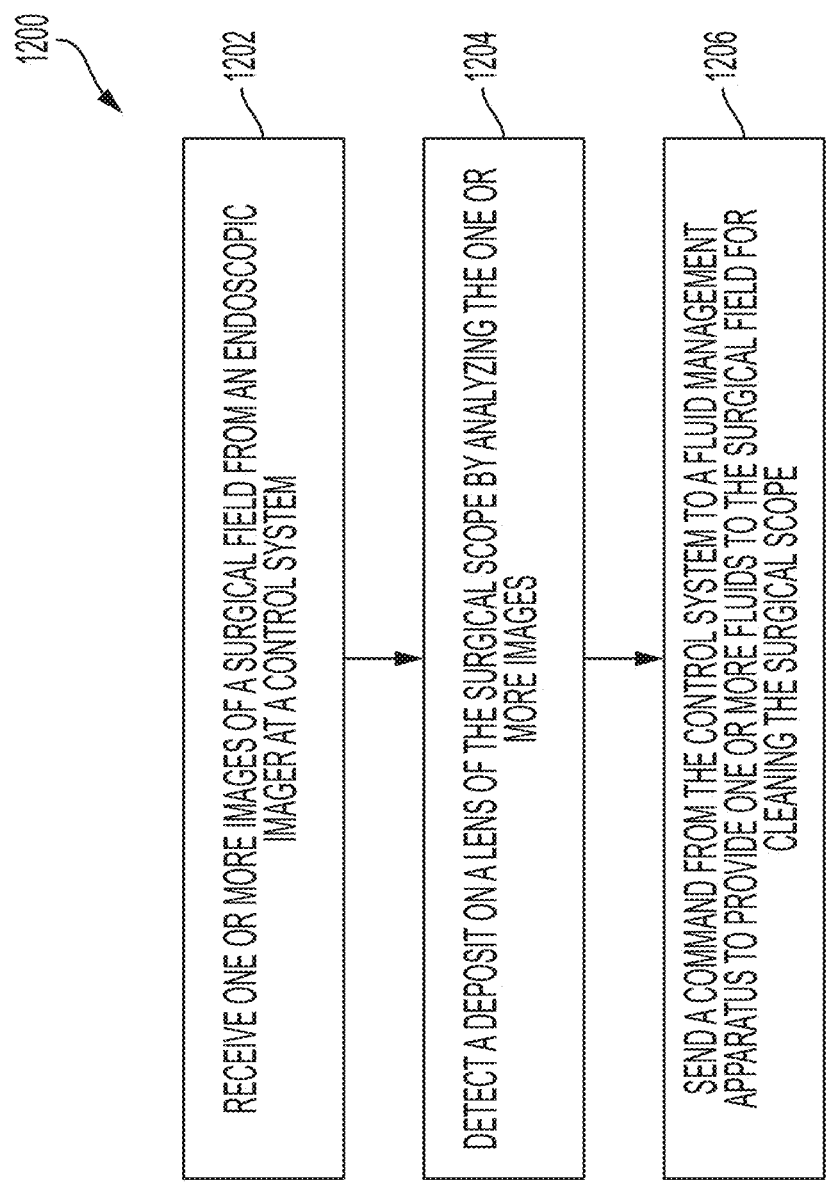
FIG. 12 illustrates a method for automatically detecting deposits on a lens of a surgical scope and sending a command to a connected apparatus to initiate a cleaning sequence for the surgical scope, according to various embodiments.

FIG. 11B illustrates a perspective view of a cross-section (taken on line A-A of FIG. 11A) of a portion of the shaft 1102 of scope 1100. The shaft 1102 includes at least one fluid channel 1120 for fluid to flow between the at least one fluid port 1110 in the main body 1104 and the at least one fluid outlet 1114 at the distal end 1116 of the shaft 1102. The at least one fluid channel 1120 is located between a first wall portion 1122 that corresponds to the outer tubular wall of a conventional scope shaft (see tube 152 of scope 150 of FIGS. 1A-1B for an example of an example of an outer tubular wall of a conventional scope configuration) and a second wall portion 1130 that extends at least partially around the first wall portion 1122.

According to various embodiments, the second wall portion 1130 extends only partially around the first wall portion 1122 such that the external surface of the shaft 1102 is formed by the second wall portion 1130 and the portion of the first wall portion 1122 that is not surrounded by the second wall portion 1130. With the second wall portion 1130 extending only partially around the first wall portion 122, the outer surface of the shaft 1102 is non-cylindrical. The increase in size needed to accommodate the at least one fluid channel 1120 is concentrated in a width 1134 of the shaft 1102 in the direction of the major axis, with the increase in width 1132 in the direction of the minor axis being less or none at all relative to the shaft of a conventional endoscope of the same size. In some embodiments, the first wall portion 1122 is cylindrical and the width 1132 of the shaft 1102 in the direction of the minor axis is equal to the diameter of the first wall portion 1122, such that there is no increase in width of the shaft 1102 along the minor axis relative to a conventional scope shaft of the same size. For example, the width 1132 along the minor axis for an endoscope 1100 sized to correspond to a conventional 4 mm scope may be 4 mm.

According to various embodiments, the first wall portion 1122 and second wall portion 1130 are integrated into a unitary piece, which can be formed in any suitable fashion, such as via welding the second wall portion 1130 to the first wall portion 1122, extrusion, and/or machining. In some embodiments, multiple fluid channels are provided between the first wall portion 1122 and the second wall portion 1130, such as configured like the two conduits 118 and 120 shown in FIG. 1D.

The shaft 1102 includes an inner tube 1124 that is located radially inwardly of the first wall portion 1122 and defines with the first wall portion 1122 a channel 1126 for locating fiber optics that carry light from a light cable connected to the light port 1108. The inner tube 1124 defines an optical channel 1128 for directing light from a scene and can house one or more optical components (not shown).

Figure 11D:
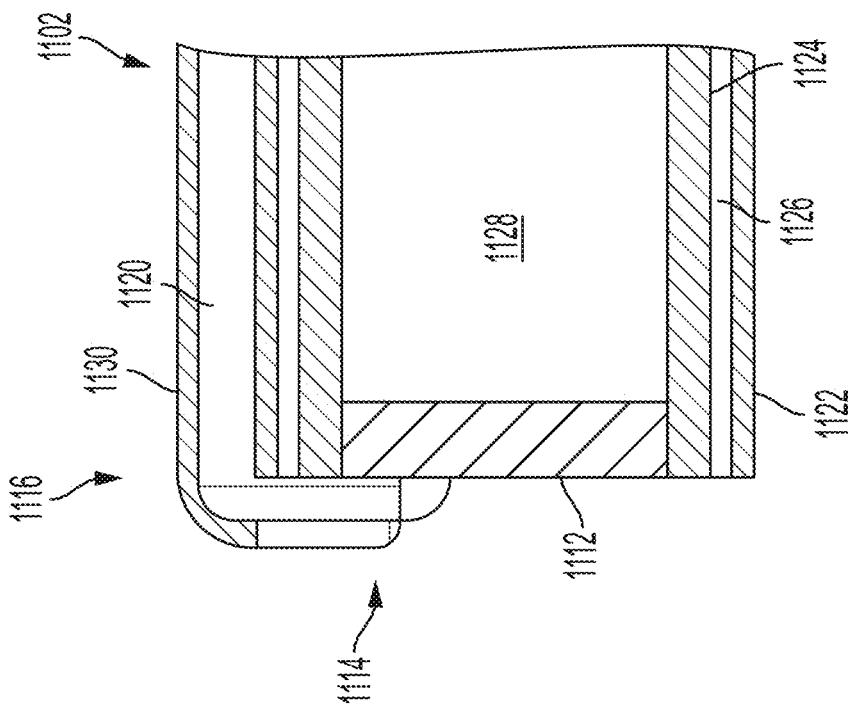
FIGS. 11C and 11D are perspective and cross-sectional views, respectively, of a distal portion of a scope with integrated cleaning, according to some embodiments.
Figure 11C:
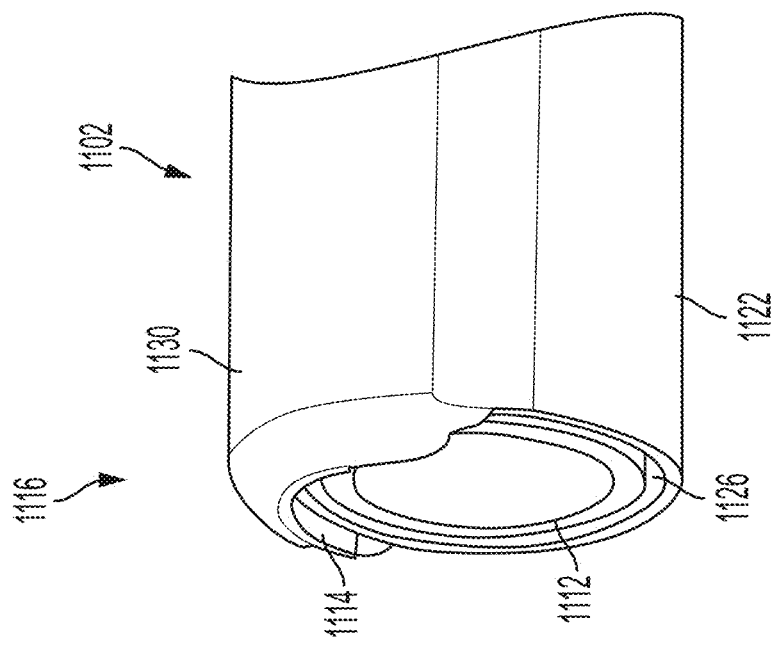

FIGS. 11C and 11D are perspective and cross-sectional views, respectively, of a distal portion of the shaft 1102, according to various embodiments. At least one fluid outlet 1114 is provided at the distal end 1116 of the shaft 1102 and is configured for directing fluid from the at least one fluid channel 1120 onto an optical component 1112 located at the distal end of the 1116 of the shaft 1102. The at least one fluid outlet 1114 is configured to turn the fluid flow so that it impinges on the optical component 1112 to wash and/or blow deposits from the optical component 1112. In some embodiments, the at least one fluid outlet 1114 is formed by rolling a distal end of the second wall portion 1130 inwardly. In some embodiments, a separate fluid outlet 1114 is joined to the distal end of the second wall portion 1130. In some embodiments, the at least one fluid outlet is rigidly disposed on the shaft 1102 to ensure that the at least one fluid outlet does not obscure the field of view of the endoscope 1100. The at least one fluid outlet can be configured to minimize reflections, such as by being provided with a non-reflective coating or formed of a non-reflective material.

In some embodiments, a fluid outlet can be provided for each of multiple fluid conduits. For example, multiple fluid outlets could be configured as in nozzle head 110 of FIG. 1C, which includes two nozzles 112, 114. In some embodiments, a single fluid outlet can be provided for multiple fluid conduits. The single fluid outlet can be configured for providing fluids from the multiple conduits sequentially—such as a liquid spray followed by a gas blow—and/or for providing a mixture of the fluids from the multiple conduits.

Figure 11E:
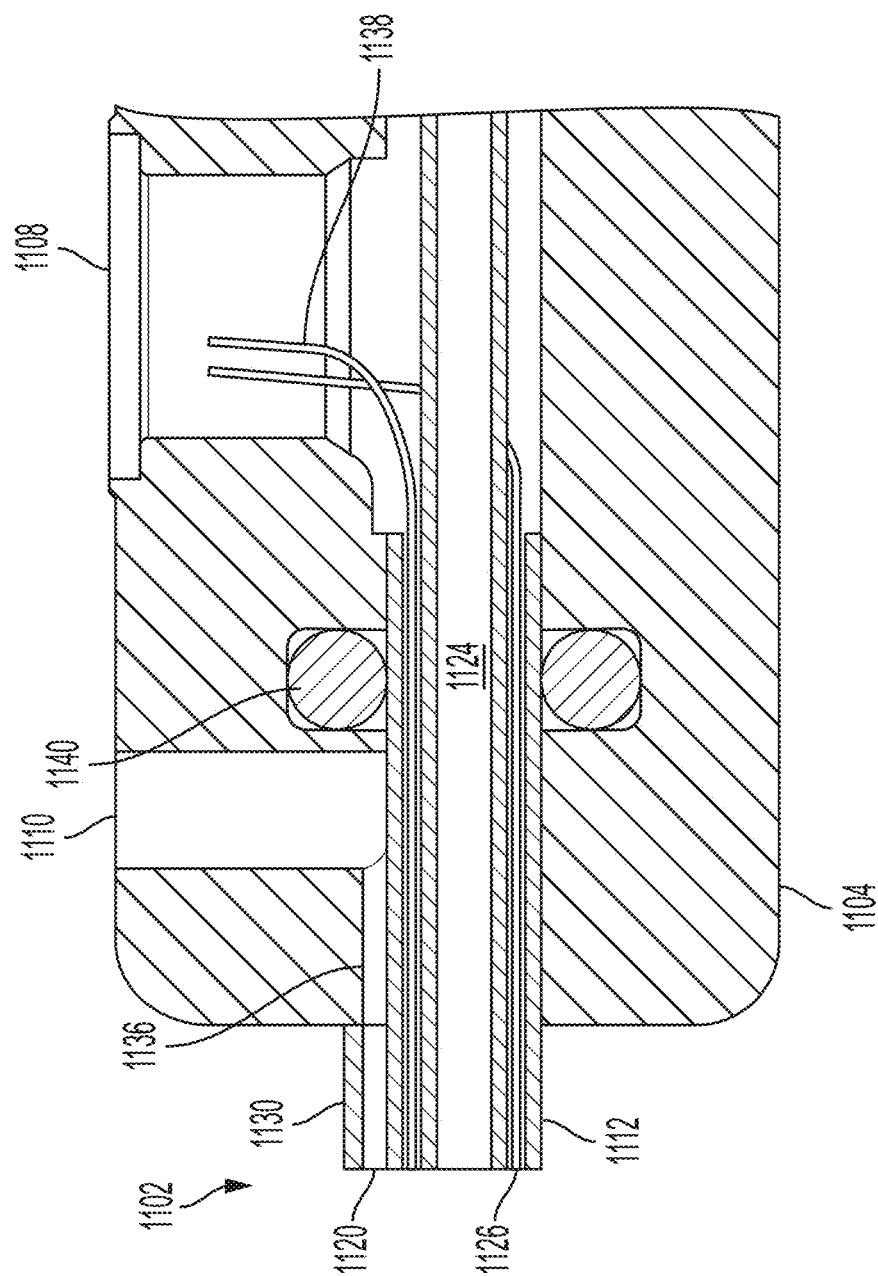
FIG. 11E is a cross section of a proximal portion of a shaft and a portion of a main body of a scope with integrated cleaning, according to some embodiments.

FIG. 11E is a cross section of a proximal portion of the shaft 1102 and a portion of the main body 1104, according to some embodiments. The at least one fluid port 1110 communicates with the at least one fluid channel 1120 of the shaft 1102 via a fluid passageway 1136 in the main body 1104. In some embodiments, the fluid passageway 1136 is defined by a gap between the first wall portion 1122 and an opening in the main body 1104 formed for receiving the first wall portion 112.

The second wall portion 1130 can be sealed to the main body 1104 to prevent fluid leakage, such as by welding the second wall portion 1130 to the main body 1104. In some embodiments, the second wall portion 1130 terminates at the main body 1104.

According to some embodiments, the first wall portion 1122 extends into the main body 1104 and terminates within the main body 1104. Fiber optics 1138 from the light port 1108 extend into the channel 1126. The inner tube 1124 may extend toward the proximal end of the main body 1104, terminating at the eyepiece 1106.

According to various embodiments, to prevent fluid leakage into the optical portion of the main body 1104, a seal 1140 is positioned in the main body 1104 for sealing between the main body 1104 and the outer surface of the first wall portion 1122 at a location that is between the fluid port 1110 and the light port 1108. The seal 1140 can prevent fluid from flowing proximally into the light port portion of the main body 1104.

Endoscope 1100 can be used according to any of the methods described above, including method 900 of FIG. 9 and method 1000 of FIG. 10, except that the fluid flow and nozzles are provided directly on the endoscope 1100 rather than as part of a sheath. For example, according to various embodiments, one or more tubes of one or more fluid supply systems, such as apparatus 300 for managing fluid flow into and out of a surgical field of FIG. 3, fluid supply apparatus 400 of FIGS. 4A and 4B, fluid supply apparatus 500 of FIGS. 5A-5B, or fluid supply apparatus 600 of FIG. 6, are connected to the one or more fluid ports 1110 of the endoscope 1100. This may be done, for example, using tube set 700 of FIG. 7. The endoscope 1100 is then inserted into the patient's body. Due to the smaller size of the shaft 1102 of the endoscope 1100 relative to a cleaning sheath for the same relative size scope, smaller spaces and/or a smaller incision (for a smaller trocar) can be achieved. The endoscope 1100 can be used in a conventional manner and when deposits form on the optical component 1112, one or more fluids can be directed to the optical component 1112 to remove the deposits. The triggering of the fluid flow can be achieved in any suitable manner, including according to any of the methods described herein for sheath-based cleaning.

According to some embodiments, the endoscope 1100 is configured as a sinuscope and has a single fluid port 1110, single fluid channel 1120, and single fluid outlet 1114. The endoscope 1100 is attached to commercially available sinuscope cleaning pump(s) via tubing connected to the fluid port 1110. When the pump is activated, fluid (such as saline) flows into the fluid port 1110, flows through the fluid channel 1120, and flows onto the optical component 1112 of the endoscope 1100 to wash deposits (such as smudging or fogging) from the optical component 1112. During a reverse cycle of the pump(s), fluid can be drawn back into the fluid channel 1120 via the fluid outlet 1114 (which then functions as a fluid inlet) to remove fluid from the optical component 1112 of the endoscope 1100. According to various embodiments, the cross-sectional area of the fluid channel 1120 is optimized to prevent the development of back-pressure in the tubing while also allowing for appropriate velocity and direction of the fluid at the distal end 1116 of the endoscope 1100.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A system for cleaning a surgical scope of an endoscopic imager, the system comprising:
a fluid delivery apparatus comprising at least one controller and a value valve system for controlling supply of one or more fluids to a surgical scope cleaner fluidly connected to the fluid delivery apparatus; and
an image processing system communicatively connected to the fluid delivery apparatus, the image processing system comprising one or more processors programmed to:
receive one or more images of a surgical field generated by the endoscopic imager,
detect a deposit on a lens of the surgical scope by analyzing the one or more images,
in response to detecting the deposit on the lens of the surgical scope, provide a notification to a user that a deposit on the lens has been detected,
receive, from the user, a response to the notification confirming that the user desires cleaning of the surgical scope, and
in response to receiving the response to the notification confirming that the user desires cleaning of the surgical scope, send a command to the controller of the fluid delivery apparatus instructing the fluid delivery apparatus to provide one or more fluids to the surgical field for cleaning the surgical scope,
wherein the controller of the fluid delivery apparatus is configured to, in response to receiving the command from the image processing system, automatically control a cleaning sequence for cleaning the surgical scope.

2. The system of claim 1, wherein the apparatus is configured for supplying a liquid flow and a gas flow for cleaning the lens of the surgical scope.

3. The system of claim 1, wherein the cleaning sequence comprises supplying the liquid flow for a first period and supplying the gas flow for a second period that is at least partially subsequent to the first period.

4. The system of claim 1, wherein the image processing system is configured for analyzing the one or more images at least partially by comparing at least one of the one or more images to at least one previously generated image.

5. The system of claim 1, wherein the confirmation from the user is received from the endoscopic imager that is communicatively connected to the image processing system.

6. The system of claim 1, wherein the apparatus is configured for supplying an insufflating gas flow to the surgical field.

7. The system of claim 6, wherein the apparatus comprises:

a gas inlet port for connecting a supply line for supplying the insufflating gas to the apparatus;

a first outlet port for supplying a first flow of the gas for insufflating the surgical cavity during the surgical procedure;

an actuator for controlling a liquid flow for cleaning the surgical scope during the surgical procedure; and a second outlet port for supplying a second flow of the gas for clearing liquid from the surgical scope during the surgical procedure.

8. The system of claim 1, wherein the apparatus is configured to supply a liquid to the surgical field for cleaning the surgical scope.

9. The system of claim 8, wherein the apparatus is configured to supply the liquid to a scope cleaning sheath mounted to the surgical scope.

10. The system of claim 8, wherein the surgical scope comprises an integral fluid channel and the apparatus is configured to supply the liquid to the surgical scope.

11. A method for cleaning a surgical scope of an endoscopic imager via an image processing system that comprises one or more processors and is communicatively connected to a fluid delivery apparatus that comprises at least one controller and a valve system for controlling supply of one or more fluids to a surgical scope cleaner, the method comprising:

receiving one or more images of a surgical field from the endoscopic imager at the image processing system;

detecting by the image processing system a deposit on a lens of the surgical scope by analyzing the one or more images;

in response to detecting the deposit on the lens of the surgical scope, providing a notification to a user that a deposit on the lens has been detected;

receiving, from the user, a response to the notification confirming that the user desires cleaning of the surgical scope;

in response to receiving the response to the notification confirming that the user desires cleaning of the surgical scope, sending a command from the image processing system to the controller of the fluid delivery apparatus instructing the apparatus to provide one or more fluids to the surgical field for cleaning the surgical scope; and in response to the controller of the fluid delivery apparatus receiving the command from the image processing system, automatically controlling a cleaning sequence for cleaning the surgical scope.

12. The method of claim 11, wherein automatically controlling the cleaning sequence comprises supplying a liquid flow and a gas flow from the apparatus for cleaning a lens of the surgical scope.

13. The method of claim 12, wherein supplying the liquid flow and the gas flow comprises supplying the liquid flow for a first period and supplying the gas flow for a second period that is at least partially subsequent to the first period.

14. The method of claim 11, wherein the confirmation from the user is received from the endoscopic imager that is communicatively connected to the image processing system.

15. The method of claim 11, further comprising supplying an insufflating gas flow from the apparatus to the surgical field.

16. The method of claim 11, wherein the one or more fluids comprises a liquid and the method further comprises providing the liquid to the surgical field for cleaning the surgical scope.

17. The method of claim 16, wherein the surgical scope is mounted to a scope cleaning sheath that receives the liquid.

18. The method of claim 16, wherein the surgical scope comprises an integral fluid channel.

* * * * *